Figure 1:
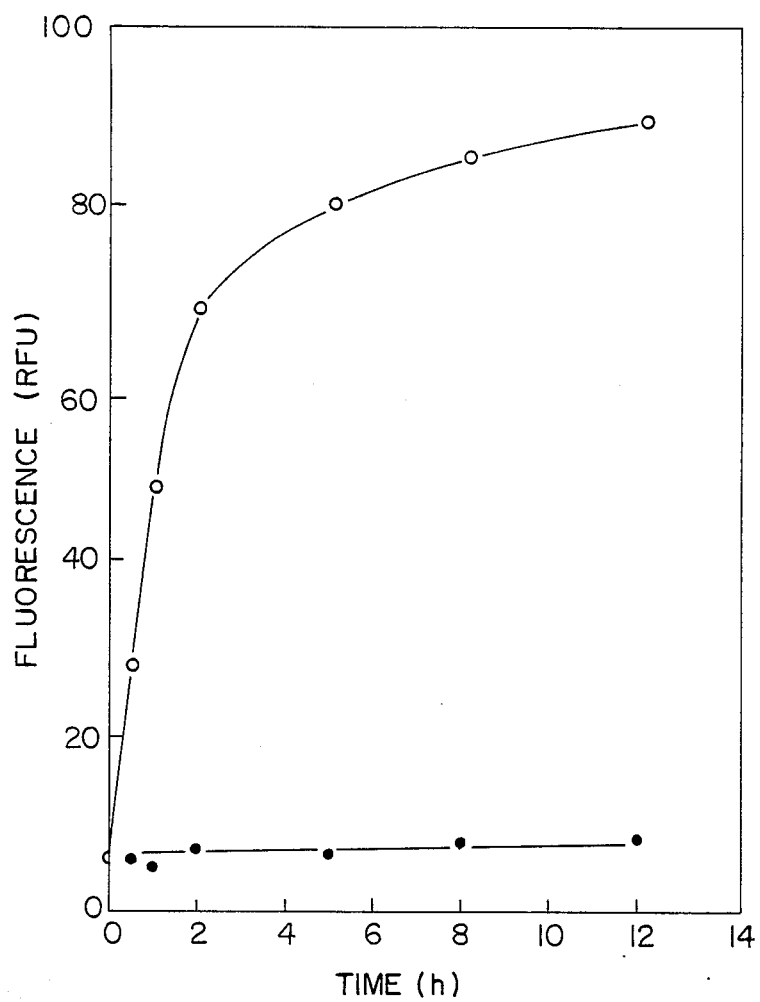

United States Patent [19]

Brynes et al.

[11] Patent Number: 4,897,444
[45] Date of Patent: Jan. 30, 1990

[54] IMMOBILIZED FLUOROGENIC SUBSTRATES FOR ENZYMES; AND PROCESSES FOR THEIR PREPARATION

[75] Inventors: Paul J. Brynes, Libertyville, Ill.; Patricia Andrade-Gordon, Port Jefferson, N.Y.

[73] Assignee: The Research Foundation of the State University of New York, Albany, N.Y.

[21] Appl. No.: 740,706

[22] Filed: Jun. 3, 1985

Related U.S. Application Data

[63] Continuation-in-part of Ser. No. 739,746, May 31, 1985, abandoned.

[51] Int. Cl.$^4$ .............................................. C08L 89/00
[52] U.S. Cl. ..................................... 525/54.1; 435/23; 435/24; 530/330; 530/331; 530/300
[58] Field of Search .................... 530/380, 330, 331; 525/54.1; 435/23, 24

[56] References Cited

U.S. PATENT DOCUMENTS

| | | |
|---|---|---|
| 3,884,896 | 5/1975 | Blomback et al. |
| 3,886,136 | 5/1975 | Claeson et al. |
| 4,016,042 | 4/1977 | Svendsen . |
| 4,070,245 | 1/1978 | Svendsen . |
| 4,081,329 | 3/1978 | Jaworek et al. ................... 525/54.1 |
| 4,188,264 | 2/1980 | Iwanaga et al. |
| 4,326,008 | 4/1982 | Rembaum .......................... 525/54.1 |

OTHER PUBLICATIONS

Paul J. Brynes et al., "6-Aminoquinoline as a Fluorogenic Leaving Group in Peptide Cleavage Reactions: A New Fluorogenic Substrate for Chymotrypsin[1]", *Analytical Biochemistry* 116, 408–413 (1981).

Paul J. Brynes et al., "Sensitive Fluorogenic Substrates for the Detection of Trypsinlike Proteases and Pancreatic Elastase", *Analytical Biochemistry* 126, 447–455 (1982).

Patricia Andrade-Gordon et al., "Synthesis and Kinetic Studies of Protease Substrates Containing the 1-Methyl-6-Aminoquinolinium Ion as A Fluorogenic Leaving Group", *Journal of Medical Chemistry* 27, 1166 (1984).

*Primary Examiner*—Sam Rosen
*Attorney, Agent, or Firm*—Morgan & Finnegan

[57] ABSTRACT

An immobilized fluorogenic substrate useful in processes for identifying and quantifying, intra- and extracellularly, and mammalian body fluids, as well as animal cell abstracts is disclosed. The immobilized fluorogenic substrate has the structure

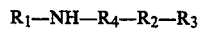

$$R_1-NH-R_4-R_2-R_3$$

wherein $R_1$ represents an enzyme-specific oligopeptide; $R_2$ represents a spacer group which is methylenecarbonyloxy, a methylenecarboxamido, or a methylanesulfonamido group attached to a polymethylene chain which itself has a functional group suitable for coupling with a polymer; $R_3$ represents a biologically inert polymer; and $R_4$ represents a fluorogenic moiety.

11 Claims, 3 Drawing Sheets

IMMOBILIZED FLUOROGENIC SUBSTRATES FOR ENZYMES; AND PROCESSES FOR THEIR PREPARATION

This application is a continuation-in-part of U.S. Ser. No. 739,746 filed May. 31, 1985, now abandoned.

BACKGROUND OF THE INVENTION

1. Field of The Invention

This invention relates to new immobilized substrates and processes for their preparation and use in identifying and quantifying production and/or secretion of an enzyme specific to a cell type.

2. Description of Prior Art

A considerable body of research has centered on improving the early diagnosis of invasive and degenerative diseases such as cancer, arthritis and pulmonary emphysema. Standard methods for determining identities of pathogenic bacteria associated with infections are lengthy and often entail a wait of up to two days after taking cultures. These diseases involve synthesis and secretion by tissues of proteolytic enzymes (proteinases) that are capable of catalyzing the breakdown of proteinaceous materials. In cancer primarily connective tissues (collagen, elastin, etc.) which are hydrolyzed, and thus degraded, during the processes of tumor invasion and metastasis, or during the degradation of pulmonary alveolar membranes. In arthritis, articular cartilage surfaces are eroded enzymatically by the action of a variety of proteases collectively known as collagenases. A broad range of bacterial cells secrete other proteinases that are used to destroy antibodies produced and employed by the body to limit the invasion of microbes.

Uncontrolled destruction of intra- or extracellular proteins by proteinases is associated with many pathological conditions such as the breakdown of articular cartilage by elastase during rheumatoid arthritis, the destruction of pulmonary elastin by elastase during emphysema, and the activation of plasminogen during the invasion of healthy tissues by tumor cells. Proteolytic enzymes also play a role in rotavirus infectivity and are important for rotavirus propagation.

Proteolytic enzymes are involved in loss of growth regulation, invasiveness, metastasis, and formation of malignant tumors. Although tumor cells produce a wide variety of proteinases, the occurence of high levels of plaminogen activator (PA) is uniquely associated with malignancy. Elastase, a serine proteinase has been isolated and characterized from the human granulocyte (PMN). This enzyme is responsible for the release of proteoglycan matrix from intact articular cartilage and can degrade isolated aggregates or subunits of proteoglycan in solution. Elastase also stimulates cellular migration to the site of inflammation, can cleave intermolecular cross links of collagen, and can also cleave the helical portion of collagen III and IV. The latter action of elastase could be of the utmost importance in tissue damage. It is of great importance then to characterize the proteinase active in the acute response to inflammatory disease. Although similar proteinase activity is found in macrophages and in neutrophils, the major natural proteinase secreted by activated or inflammatory macrophages is plaminogen activator while elastase is most probably the key enzyme in neutrophil mediated proteolysis.

Simple synthetic substrates in which only one bond is susceptible to enzymatic hydrolysis often are used to assay serine proteinases. Most often, esters of L amino acids blocked at the N terminal are used. Ester substrates have the advantage over the corresponding amides in that Km values are lower and catalytic rate constants are higher. However, esters present difficulty in measuring the products of hydrolysis, i.e., the alcohol and the free amino acid. They also are not as well-selectively distinguished in the process of enzyme recognition. For example, Visser et al., 268 Biochim. Biophys. Acta 257 (1972) introduced the use of Boc-Alanyl-p-nitrophenyl ester as a substrate for elastase. However, it is also susceptible to hydrolysis by trypsin and chymotrypsin, is poorly water soluble and undergoes considerably spontaneous hydrolysis at pH 8.0. The acetyl-(alanine)$_3$-methyl ester substrate that was proposed by Gertler et al., 48 Canad. J. Biochem. 384 (1970) overcomes most of these disadvantages, but its enzymatic hydrolysis must be monitored by time consuming potentiometric methods. The general applicability of esterolytic assays has been limited.

Studies of the action of a proteinase on small natural peptides of known sequences also have been useful in obtaining a broad characterization of the enzyme in question. The oligopeptides obtained, after proteolytic digestion under controlled conditions, are separated and identified.

For measurement of general proteolytic activity, the method of Kunitz, 22 J. Gen. Physiol. 429–446 (1939) is usually applied. This method uses casein as the substrate and a spectrophotometric method which depends upon differences in absorption between the products of hydrolysis and the substrate. The rate of change in absorption at a selected wavelength is proportional to the rate of hydrolysis.

Erlanger et al., 3 Biochemistry 346 (1961) describe the use of the p-nitroanilide of N benzylarginine (BAPNA) as a substrate for trypsin like proteinases. Colorimetric assays employing this substrate have two major or advantages over previous assays. First, the bond that is cleaved is an amide bond. Selectivity of proteolytic enzymes is much better for amide bonds than ester bonds. Second, the p-nitroanilide derivative is a chromogenic substrate. When it is cleaved by the enzyme, p-nitroaniline is released, which has a strong ultraviolet absorption at a different wavelength from that of the substrate. p-Nitroaniline is an aromatic amine with an extinction coefficient of 8,800 at 410 nm (Erlanger et al., supra). This compound, however, cannot be detected below $10^{-7}$ M unless it is converted by diazo coupling into a derivative having a stronger chromphore (Bieth et al., 53(2) Biochem. Biophys. Res. Comm. 383390 (1973)).

Fluorogenic substrates for proteinases have recently drawn considerable attention because they are capable of lowering the limit of detection obtainable from peptidyl p-nitroanilide substrates by as much as two orders of magnitude. The fluorogenic portion is generally an acylated aromatic amine. Upon hydrolysis, the spectroscopic properties of the leaving groups usually shift to longer wavelengths of absorption and/or emission, that are characteristic for the particular fluorophore.

Zimmerman et al., 70 Anal. Biochem. 258–262 (1976) describe the use of the fluorogenic substrate, 7 -glutaryl phenylalanylamido-4-methylcoumarin as a stable amide substrate for chymotrypsin. The sensitivity of this substrate is due to the fact that the leaving group, 7-amino-4 -methylcoumarin (AMC), is highly fluorescent. The amides are stable in solution and are in addition more closely related to the natural substrates. In a later study (Zimmerman et al., 78 *Anal. Biochem,* 47-51 (1977)), the preparation and use of fluorogenic amide using aminocoumarin as the leaving group was described for trypsin and elastase.

Castillo et al., 99 *Anal. Biochem.* 53-64 (1979) reported different substrates in which the leaving group was varied. The sequence used for the peptide was MeOSuc-Ala-Ala-Pro-Val-X, which had been shown to be highly reactive and relatively specific toward human leukocyte elastase (HLE). The X in the sequence represented 4-nitroanilide ( NA), thiobenzyl ester (-SBzl), 4-methyl-7-aminocoumarylamide (-AMC), or 1-methoxy-3-naphthylamide (-NNapOMe). The thiol benzyl ester substrate was shown to be the best of the series. Advantages of this substrate are its high kcatKm values and ease of synthesis. However, there is often interference from high concentrations of thiols present in samples such as cellular extracts or culture media. The peptidyl-AMC substrates are as sensitive as the thiol benzyl ester. They are, however, more difficult to synthesize and have lower kcat/Km values. The enzymatic cleavage does, in this case, involve a peptide linkage. However, for a rate assay, it had a lower sensitivity than either the thiobenzyl ester or peptidyl-AMC.

The following patents and reports also describe the use and application of solution chromogenic substrates: U.S. Pat. Nos. 3,884,896; 3,886,136; 4,016,042; 4,070,245 and 4,188,264; Plapinger et al 30 *J Org Chem.* 1781-1785 (1965) and Nachlas et al., 108 *Arch. Biochem. Biophys.,* 266-274 (1964).

An assay for proteinases based on the fluorescent labeling of insoluble proteins (fibrin) or of soluble casein was described by Wiesner et al., 121 *Anal. Biochem.* 290-294 (1082). The fluorogenic reagent 2-methoxy-2,4-diphenyl-3(2H)-furanone (MDPF) was used to label the proteins. Fluorescence of the liberated peptide fluorophore conjugates resulting from enzymatic hydrolysis was measured in the supernatant after separation of the unreactive casein-fluorophore by acid precipitation. However, the enzymatic hydrolysis cannot be followed continuously during the time of incubation since interruption of the reaction is necessary for removal of the supernatant products.

Dipeptide derivatives of rhodamine were reported by Leytus et al., 215 *Biochem. J.* 253-260 (1983) as having a high degree of sensitivity and selectivity.

Synthetic chromogenic or fluorogenic substrates composed of peptidyl amides of aromatic amines have been widely used to detect and quantify proteinases and to define their amino acid specificities (Knight, *Proteases in Mammalian Cells and Tissues,* North Holland Pub. Co Amsterdam 1977)). Because of the sensitivity of fluorimetry, fluorogenic substrates are particularly suitable as probes of enzyme structure and mechanism. A number of problems, however, are generally encountered that limit the use of these agents.

First, the fluorescence spectra of the substrate and product often overlap to a significant degree, and it becomes necessary to use wavelengths longer than the excitation maximum to excite the product in order to avoid high levels of background emission from the excess unhydrolyzed substrate. This compromise decreases the fluorescence intensity used to estimate product, thereby lowering the sensitivity of the assay. For example, fluorogenic leaving groups such as β-naphthylamine and 7-amino-4-methylcoumarin can be detected at nanomolar concentrations, yet this limit is not often achieved experimentally under assay conditions. If the spectrofluorimeter is adjusted to monitor the appearance of the product at its fluorescence maximum, high levels of background emission are produced by the large excess of substrate and it becomes exceedingly difficult to measure accurately the amount of amine liberated early in the course of substrate hydrolysis. Consequently, it is rare that both excitation and emission maxima can be selected for fluorescence studies of this type. Instead, a compromise must be reached between decreased background fluorescence at the expense of operating in the lower fluorescence spectral region of the product.

Second, the aromatic amines are usually hydrophobic and thus require organic cosolvents (e.g., dimethylformamide or dimethyl sulfoxide) to solubilize them. The presence of these solvents can produce unpredictable inhibitory or stimulatory effects on the enzyme. In addition, such solvents are inappropriate for the in situ assay of proteinases in cell culture.

Third, the currently available chromogenic or fluorogenic groups are not readily amenable to derivatization. A leaving group of the substrate should be readily derivatized into series of congeners which allow studies of the steric and electronic requirements of the active site of the enzyme. Moreover, derivatization of this sort permits the possibility of immobilizing the fluorogenic moiety on solid supports via covalent bond formation.

Fourth, these compounds are not conveniently used for the assay of single cells. Several laboratories have explored the application of chromogenic peptides as histochemical probes for revealing the presence of peptidase activity in cells (Dolbeare et al., 27(11) *J. Histochem. Cytochem* 1493-1495 (1979); and Sannes et al., 27 *J. Histochem. Cytochem* 1496-1497 (1979)); and tissue sections (Blasini et al., 13 *Thrombosis Rev.* 585-590 (1978); and Grabske et al., (11) *J. Histochem. Cytochem.* 1505-1508 (1979)). Although these substrates are selective reagents for the quantitation of various proteinases, a major shortcoming is that they are only practical for the assay of proteinases released into the extracellular medium by a population of cells. Another disadvantage of these cytochemical methods is that the low concentration of chromopore that is liberated by cellular proteinases is difficult to detect, and hence, it must often be visualized by conversion, using an azocoupling reaction, into derivatives having larger extinction coefficients. Unfortunately, the vigorous conditions needed to affect this transformation preclude its use with cells and tissues where one wishes to maintain viability.

Recently, a fluorescent proteinase transition state analog-inhibitor, dansyl-L-arginal (DansArgH) was introduced as a selective probe for cysteine and serine type proteinases in a fibrosarcoma tumor cell line (Kozlowski et al., 81 *Proc. Nat'l. Acad. Sci.* 1135-1139 (1984)). However, the conditions used to quantify and to visualize enzyme activity also prevented the maintenance of cell viability.

Fifth, a drawback of low molecular weight substrates is that they diffuse from the site of reaction, even if entrapped within an agarose or gelatin matrix. This limits their application as probes of proteinase activity in single-cells. As a result, only very brief exposure periods can be employed if enzyme activity is to be localized at an individual cell or discrete tissue region. These restrictions diminish the sensitivity of such methods and confine application to cells which secrete relatively large amounts of proteinase. Similar limitations also are encountered when radiolabeled substrates dried onto the surface of microtiter wells are used as an assay for proteolytic activity (Varani et al., 107 *Anal. Biochem.* 377–384 (1980)). Besides the usual disadvantage of handling radioactive materials, one cannot localize the regions of proteolytic activity since the radioactive product of the reaction is released into the supernatant fluid.

Sixth, a disadvantage of currently used proteinase detection methods concerns quantitative. Individual cells that secrete specific proteinases have been identified by techniques that involve the formation of a pericellular lysis zone in an opalescent agar matrix containing a natural substrate such as fibrin or casein (Jones et al., 5 *Cell.* 323–329, (1975)). Although this type of assay is sensitive, it is not quantitative because the relationship between the size of the lysis zone and the amount of enzyme in question is not known. Moreover, the agar matrix used in the system is not physiological and therefore some cells do not survive this treatment. Also, this technique can only be used for cells that grow in soft agar and it is capable of detecting only those enzymes that digest the macromolecular substrates.

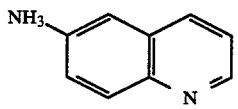

has been introduced (Bryness et al., 116 Anal. Biochem. 408–413 (1981)) as an exceptionally useful fluorogenic group for synthetic substrates because: (a) it is approximately the same size as, β-naphthylamine,

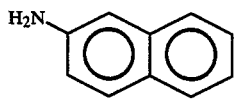

a fluorogenic moiety commonly used in proteinase substrates; (b) after alkylation of the ring nitrogen, it has a similar distribution of charges as the p-nitroaniline leaving group,

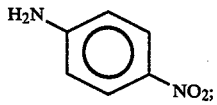

(c) acylaminoquinolines are known to fluoresce only weakly in the bluish-white region of the spectrum, whereas the free amine emits intensely yellowish green light (the part of the visual spectrum in which the eye is most sensitive); (d) the appearance of 6-AQ can be measured fluorometrically at its excitation and emission maxima, while at these wavelengths the substrate is essentially nonfluorescent (Brynes et al., supra, 1981); (e) the wavelength of maximal excitation of 6-AQ is sufficiently low in energy that chromophores of proteins and nucleic acids are not excited; (f) the amino group of 6-AQ can undergo acylation by peptides in high yield because it is more basic than the resonance-deactivated amino groups of other frequently used chromophores; and (g) the ring nitrogen of the quinolines is readily quaternized by a variety of alkylating agents, generating highly water soluble substrates.

SUMMARY OF THE INVENTION

1. Objects of the Invention

It is an object of this invention to provide an immobilized fluorogenic substrate suitable for identifying and quantifying both production and secretion of cell specific enzymes, intra- and extra-cellularly, in human and mammalian body fluids as well as in animal cell extracts.

An object of this invention is to provide processes for preparing the immobilized substrates of this invention.

Another object of this invention is to provide processes for using the immobilized substrates of this invention to identify and quantify production and/or secretion of cell specific enzymes.

It is an object of this invention to utilize the changes in the chromophore of a fluorogenic substrate, when hydrolyzed, for proteinase detection.

Another object is to utilize a chromophore: (a) that does not interfere with the catalytic reaction; (b) that has little or no background fluorescence at the wavelength of interest prior to cleavage; (c) such that the released amine is highly fluorescent at wavelengths where the detector has maximum sensitivity; and (d) such that the energy required to excite the chromophore is low, thus avoiding undesired photochemical reactions in biological systems.

Another object of this invention is to provide a fluorogenic substrate which has functional groups that allow the chromophore to be covalently attached to an insoluble support or to a small polymerizable molecule that can be utilized for insoluble polymer formation.

An object of the present invention is to design and synthesize oligopeptidyl amides of 6-aminoquinolines as fluorogenic substrates that undergo selective hydrolysis by specific proteinases such as plasminogen activators, elastases collagenases and the like.

Another object of this invention is to test the specificity, sensitivity and efficiency of the fluorogenic substrates by measurement of the rates of proteolysis in solution with purified enzymes.

Still another object of this invention is to covalently attach the fluorogenic moiety of the substrates to solid supports such as polyacrylamide microspheres, hydroxyethylmethacrylate gels and the like.

An object of this invention is to use immobilized fluorogenic substrates for proteolysis by quantitative fluorescence microscopy.

A further object of this invention is to utilize the immobilized fluorogenic substrates as a solid support for cell attachment and/or growth.

An object of this invention is to provide new processes for investigating in vitro detection of proteinase release by cells in culture.

These and other objects and advantages of this invention will become apparent by practice of the invention, and attained by means of the methods, processes, instrumentalities, and combinations, particularly pointed out in the amended claims.

2. Definitions

Unless otherwise stated, all amino acids used have the L-configuration, and the abbreviations have the following meanings:

Ala=alanine
Arg=arginine
Phe=phenylalanine
Pro=proline
Val=valine

Further abbreviations used are:

Ac=Acetyl
AcOH=Acetic Acid
AllylAQ+=1-allylaminoquinolinium ion
AMC=7-amino-4-methylcoumarin
6-AQ=6-aminoquinolines
Bz=Benzoyl
Bz-Val-Gly Arg-6AQ=6-(N-benzoyl-L-valyl-glycyl-L-arginylamino) quinoline
Cbz=carbobenzoxy
Cbz-Ala-Ala-6AQ=6-(N-carbobenzoxy-L-alanylamino) quinoline
Cbz-Ala-Ala-Pro-Val-6AQ=6-(N-carbobenzoxy-L-alanyl-L-alanyl-L-prolyl-L-valylamino) quinoline
γGFx=Gamma Globulin Fraction
HEMA=2-hydroxyethyl methacrylate
HLE=Human Leukocyte Elastase
IMR-90=Human Embryonic Lung Fibroblasts
LLCPK-C4=Porcine Kidney Cells
MAQ+=1-methylaminoquinolinium ion
βNA=β-Naphthylamine
pNA=p-nitroaniline
PA—Plasminogen Activator
Suc-Ala-Ala-Ala- 6AQ=6-[N-(succinylamido)-L-alanyl-L-alanyl-L-alanylamino]quinoline 3. Brief Description of The Invention The aforementioned problems associated with the currently available methods for the detection of proteinases are overcome by the applicants' invention. According to this invention, there are provided novel immobilize fluorogenic substrates whose spectroscopic fluorescence absorption and emission maxima shift to longer wavelength when the peptid moiety is enzymatically cleaved.

The immobilized substrates of this invention may be prepared by linking the initial fluorogenic substrate (peptide-fluorophore assembly) via a spacer directly and covalently (a) to an insoluble biologically inert polymer or (b) to a small inherently polymerizable molecule that can be used to generate the insoluble polymer by copolymerization with a monomer.

In one aspect, this invention relates to an immobilized fluorogenic substrate for identifying and quantifying, intra- and extra-cellularly, the production and secretion of cell specific enzymes in human and mammalian body fluids as well as in animal cell extracts, which has the structure:

wherein $R_1$ represents an oligopeptide which has a amino acid sequence that is enzyme specific in terms of cleavage at the peptide linkage proximal to the fluorogenic moiety;

$R_2$ represents a spacer group which is a methylenecarbonyloxy, a methylenecarboxamido or a methylenesulfonamido group attached to a polymethylene chain which itself has an ω-amino, ω-hydroxyl or ω-carboxylic acid or other function suitable for coupling with a polymer;

$R_3$ represents a biologically inert polymer having a complementary group (i.e., a carboxylic acid or hydroxyl or amino group) which forms an ester or amide linkage with the ω-function of the spacer moiety; and $R_4$ represents a fluorogenic moiety bearing the amino group and having a second functional group to which is attached the spacer group. $R_4$ preferably is an aminoquinolines and for purposes of illustrating this invention, the description which follows will be directed to a particular aminoquinolines, namely 6-aminoquinoline. Other chromophores can be utilized according to applicants' invention through suitable adaptations of the general principles described herein.

In another aspect, this invention relates to a process for preparing an immobilized fluorogenic substrate capable of identifying and quantifying, intra and extra cellularly, the production and secretion of cell-specific enzymes in human and mammalian body fluids as well as in animal cell extracts which comprises:

(a) coupling an enzyme-specific oligopeptide to the primary amino group of a fluorescent aminoquinolines via an amide linkage;

(b) quaternized the ring nitrogen of the quinoline moiety with an alkylating spacer group selected from halo-acetylamino, halo-acetoxy- or halomethysulfonylamino-polymethylene compounds having an ω-amino (protected), an ω-hydroxyl, or an ω-carboxylic acid group or other suitable group;

(c) coupling the ω-functional group of a spacer moiety with the complementary group of the polymer material (solid support) to form an ester or an amide linkage, which intrinsically immobilizes the peptidyl quinoline assembly.

In still another aspect, the invention relates to a process for preparing an immobilized fluorogenic substrate capable of identifying and quantifying, intra- and extra-cellularly, the production and secretion of cell-specific enzymes in human and mammalian body fluids as well as in animal cell extracts which comprises:

(a) coupling an enzyme-specific oligopeptide to the primary amino group of a fluorescent aminoquinolines via an amide linkage to form an enzyme cleavable substrate;

(b) coupling the ω-carboxylic acid group of a spacer arm to a functional group of a polymer material, the functional group being selected from an amino, hydroxy, thiol or primary amido group; and (c) coupling the product of step (b) with the enzyme-cleavable substrate by quaternized the ring nitrogen of the quinoline moiety with the alkylating terminus of the spacer arm, which intrinsically immobilizes the peptidyl quinoline assembly.

This invention also relates to a process for preparing an immobilized fluorogenic substrate capable of identifying and quantifying, intra- and extra cellularly, the production and secretion of cell specific enzymes in human and mammalian body fluids as well as in animal cell extracts which comprises:

(a) coupling an enzyme specific oligopeptide to the primary amino group of a fluorescent aminoquinolines via an amide linkage;

(b) quaternized the ring nitrogen of the quinoline moiety with an alkylating spacer group selected from haloacetylamino, haloacetoxy- or halomethylsulfonylamino-polymethylene compounds having an ω-amino (protected), an ω-hydroxyl, an ω-carboxylic acid group or other suitable group;

(c) reacting the product of step (b) with an allyl amine using a mixed anhydride coupling technique to produce an allylic monomer; and (d) copolymerizing the allylic monomer with a second (very easily) polymerizable monomer in the presence of a radical-generating catalyst, to immobilize the enzyme cleavable substrate.

In yet another aspect, this invention relates to a process for identifying and quantifying, intra and/or extra-cellularly, the production and secretion of cell specific enzymes which comprises (a) providing an immobilized fluorogenic substrate having the structure:

$R_1NH-R_4-R_2-R_3$ wherein $R_1$ represents an oligopeptide which has an amino acid sequence that is enzyme-specific in terms of cleavage at the peptide linkage proximal to the fluorogenic moiety;

$R_2$ represents a spacer group which is a methylenecarbonyloxy, a methylenecarboxamido or a methylenesulfonamido group attached to a polymethylene chain which itself has an ω-amino, ω-hydroxyl ω-carboxylic acid or other function suitable for coupling with a polymer;

$R_3$ represents a biologically inert polymer having a complementary group (i.e., a carboxylic acid or hydroxyl or amino group) which forms an ester or amide linkage with the ω-function of the spacer moiety; and $R_4$ represents a fluorogenic moiety bearing the amino group and having a second functional group to which is attached the spacer group;

(b) contacting, intra- or extra-cellularly, at least one human or mammalian test cell with the immobilized fluorogenic substrate, in an aqueous medium, the test cell being capable of producing and/or secreting a cell-specific enzyme in the aqueous medium, the fluorogenic substrate:

(i) fluorescing at a first wavelength which is an intrinsic characteristic of the fluorogenic substrate, and (ii) upon cleavage of the peptide bond proximal to the fluorogenic moiety by a cell-specific enzyme, fluorescing at a second wavelength which is an intrinsic characteristic of the cleaved substrate;

(c) measuring the intensity of fluorescence produced over a period of time by said test cell, as a function of the production and/or secretion of the cell-specific enzyme by the test cell; and (d) comparing said measurement with a measurement of fluorescence produced by a normal cell or a second test cell when placed in contact with the immobilized test substrate, the difference in said measurements being indicative of the production and/or secretion of enzymes specific to a cell type, by the test cell.

The immobilized substrates of this invention may be prepared according to one of the following three reaction sequences:

Reaction Sequence I

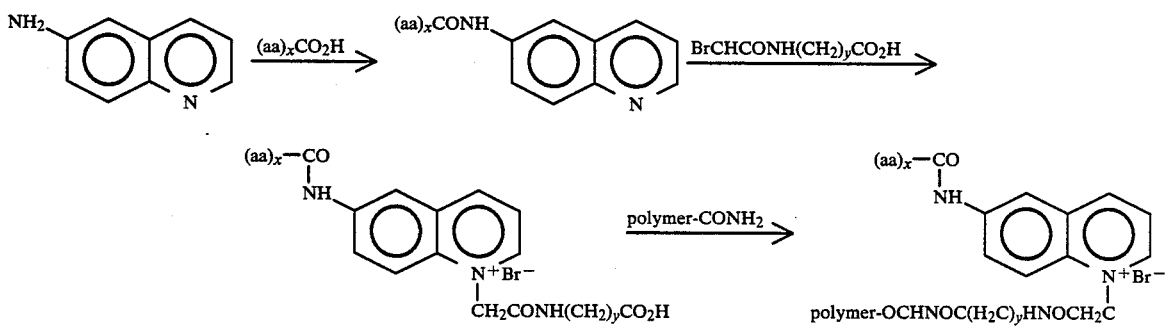

Reaction Sequence II

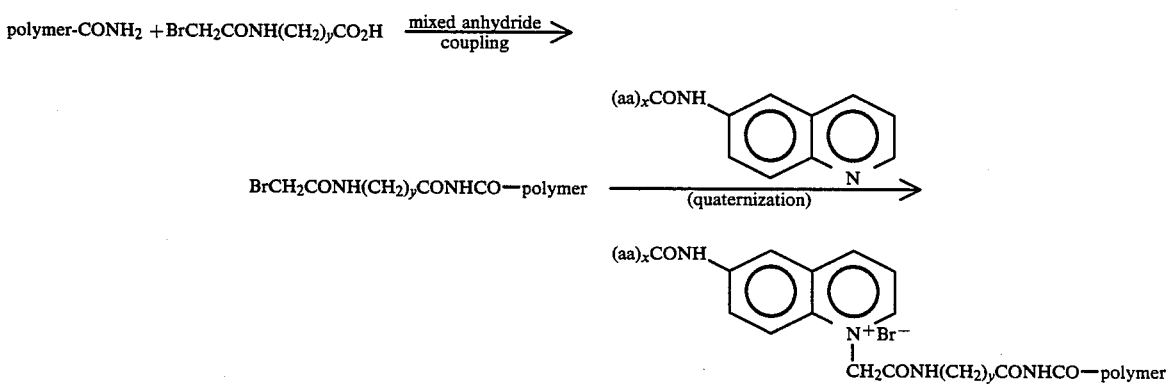

Reaction Sequence III

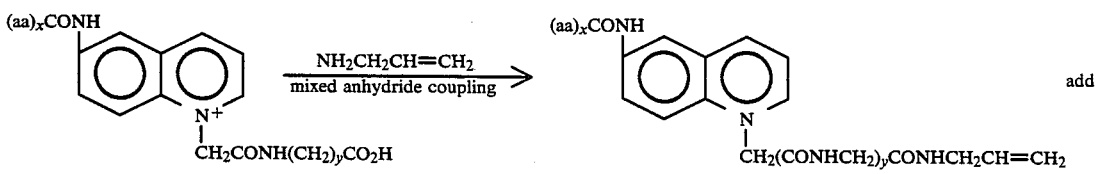

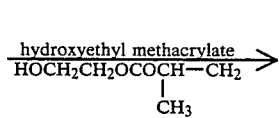 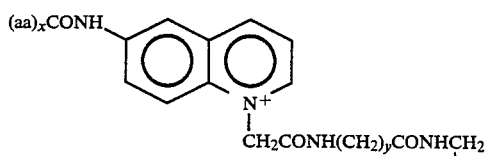

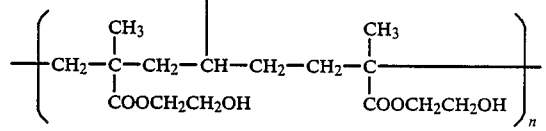

x is an integer between 1 and 6; y is an integer between 1 and 15; n is an integer greater than 2 and sufficiently large so that the polymer is present as a gel or as a solid.

Suitable oligopeptides ($aa_x$ in the above reactions according to applicants' invention) include the following sequences where X refers to any of the standard N-terminal blocking agents or H, and Y refers to a fluorescent amine:

X-valyl-proplyl-arginyl-Y;
X-(D)-phenylalanyl-picolyl-arginyl-Y;
X-phenylalanyl-valyl-arginyl-Y; X-glycyl-proplyl-arginyl-Y;
X-valyl-leucyl-lysyl Y; X-(D)-valyl-leucyl-lysyl-Y;
X-glutamyl-lysyl-lysyl-Y; X-glycyl-prolyl-lysyl-Y;
X-valyl-glycyl arginyl-Y; X-glutamyl-glycyl-arginyl-Y;
X-prolyl-phenylalanyl-arginyl-Y;
X-(D)-prolyl phenylalanyl-arginyl-Y;
X-(D)-valyl-leucyl-arginyl-Y;
X-isoleucyl-glutamyl-glycyl-arginyl-Y;
X-alanyl-prolyl-alanyl-Y; X-alanyl-alanyl-prolyl-valyl-Y;
X-alanyl-alanyl-prolyl-methionyl-Y; and the like.

Suitable spacer arms or groups according to applicants' invention are those which have a methylenecarbonyloxy, a methylenecarboxamido or a methylenesulfonamido group attached to a polymethylene chain which itself has an $\omega$-amino, $\omega$-hydroxyl, $\omega$-carboxylic acid or other function suitable for coupling with a polymer.

Preferred are those having the formula:

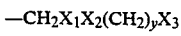

wherein:
$X_1$ is CO or $SO_2$,
$X_2$ is NH, a is zero or one, provided that when a is zero, $X_1$ is CO;
$X_3$ is NH, NHCO or CONH or OCO or COO or Si(O—)$_3$; and
y is an integer between zero and 15. Particularly preferred are:
CH$_2$CONH(CH$_2$)$_5$CONH
CH$_2$CONHCH$_2$CH$_2$NHCO
CH$_2$CONH
CH$_2$CONHCH$_2$CH$_2$CH$_2$Si(O—)$_3$
CH$_2$CONH(CH$_2$)$_5$CONHCH$_2$CH=CH$_2$ Suitable polymers according to applicants' invention include: polyacrylamide, polystyrene, (e.g., poly(4-aminostyrene) silica gel and glass (beads or plates).

Suitable monomers for polymerization with the N-allyl amides are copolymers of hydroxyethyl methacrylate, butadiene, styrene, vinyl acetate acrylic esters, acrylic amides and mixtures thereof and the like.

The fluorogenic group as illustrated in the above reactions is an aminoquinoline, but other fluorogenic groups may be employed which provides the characteristics of the aminoquinoline groups shown herein.

The fluorescent moiety in all cases has the following properties on attachment to the oligopeptide:

(1) abolition or substantial reduction of the fluorescence of the parent chromophore occurs or a shift in position of the fluorescence band occurs such that there is no interference with the fluorescent spectrum of the parent chromophore.

(2) freely diffusable into an aqueous solution, but once linked, it stays on surface of the solid support and is immobilized;

(3) when quaternized, the fluorogenic moiety is water soluble and, therefore, the kinetics of the material before and after immobilization can be correlated. Such kinetics can not be done in organic solvents.

Suitable fluorogenic moieties according to applicants' invention are believed to include aminoquinolines and their alkyl and alkoxyl derivatives; alkyl, alkoxyl, and carboxyl derivatives of aminonaphthalenes; alkyl, alkoxyl, and carboxyl derivatives of aminocoumarins; alkyl, alkoxy, amino and carboxyl derivatives of acridines; alkyl, alkoxyl, amino, nitro, and carboxyl derivatives of benzofurazans.

Preferred are the aminoquinolines such as 3-aminoquinoline (3-AQ), 2-dimethyl-aminomethyl-6-aminonaphthalene (DAN) and 4-dimethylaminomethyl-6-aminocoumarin (DAC) and particularly preferred is 6 aminoquinoline.

The preparation of 6-aminoquinoline (6-AQ) is described by Brynes et al., 116 *Anal. Biocyem.* at 409 (1981). Therein, it is disclosed that 5.0 g (28.7 mmol) of 6-nitroquinoline was added to 50 ml of a 50% aqueous solution of acetic acid. The solution was heated to 75° C., and then 4.0 g (71.7 mmol) of iron filings was slowly added during 20 min. After stirring for 90 min at this temperature, the suspension was cooled, poured over 50 g of crushed ice, and the pH adjusted to 8.5 with Na$_2$CO$_3$. The brown aqueous suspension was extracted with chloroform and the organic phases were combined, dried over magnesium sulfate, and evaporated in vacuo to afford 3.7 g of tan solids. The crude product was sublimed and recrystallized from water to yield 3.3 g (80% yield) of 6-Ag, mp 112°–113° C.

Applicants' invention allows both the detection and precise localization of proteolytic enzyme activity in biological samples. Short peptide chains bearing an amino acid sequence that mimics the region at the preferred site of the enzyme's cleavage of the natural substrate are prepared and then attached via an amide bond to a fluorescent amine, for example, 6-aminoquinoline (6-AQ). The resulting synthetic substrate, which is nonfluorescent in the regions where 6-AQ absorbs and emits, is then attached covalently via the fluorogenic amine's other chemically reactive functional group to suitably derivatized (alkylatable or acylatable) plastic, glass or other polyionic surfaces such as petri dishes, microscope slides/coverslips, or plastic or polyionic microparticulates. A sample (tissue biopsy, cultured cells or bacteria) is laid on the surface and, shortly thereafter, an intensely fluorescent zone appears at the precise location of proteolytic activity. A key aspect of the invention is that because the reagent is covalently attached to the support and cannot diffuse in solution, localization of enzymatic activity is unequivocal and defined. A wide variety of fluorescent amines can be employed because the immobilized fluorogenic substrates can be made highly selective for specific enzymes merely by varying the sequence of amino acids attached to the fluorescent amine.

According to the present invention, synthetic, fluorogenic substrates for proteolytic enzymes are prepared and chemically immobilized on an insoluble surface upon which animal or bacterial cells or tissues can be attached or grown. Therefore, the fluorescent fragment of the substrates cannot diffuse into solution either before or after their cleavage by an enzyme. The novelty of immobilization through the chromogenic group distinguishes the substrates of this invention from commercially available, soluble reagents and thereby allows the diagnosis of specific regions in tissue biopsies or even individual cells for the presence of enzymes associated with degenerative diseases, such as cancer, arthritis and emphysema. Furthermore, the new processes of this invention may be used as a rapid "typing" technique for bacteria, based on their specific proteolytic enzyme secretions, and therefore, provide a faster, more sensitive method for the identification of a patients' bacterial cultures in hospital microbiology laboratories.

The present invention makes it possible for the first time not only to study a whole range of proteolytic enzymes, but also to examine the cellular locale of protease action. Applicants' invention may be used diagnostically in clinical laboratories for the evaluation of patients' bacterial culture specimens. Virtually any proteolytic enzymes may be studied after preparation of a selective immobilized substrate for the particular enzyme, according to applicants' invention.

According to the present invention, the aforementioned problems relating to available methods to detect proteinases are overcome by the synthesis of fluorogenic substrates in which the fluorophoric moiety (e.g., 6-AQ) is covalently attached to an insoluble biologically inert polymer. In this way, the fluorescent product of the reaction cannot diffuse from the site of activation and therefore, it can be detected conveniently at any period selected using sensitive spectrofluorimetric methods. Covalently immobilized fluorogenic substrates have a potentially greater sensitivity than soluble reagents, because it is possible to achieve a high local concentration of substrate without affecting the ioic strength of the medium. Another important advantage of these agents over soluble substrates is that there can be no complications arising from possible toxicity of the fluorophore to cells or tissues. Only the oligopeptide is released from the polymeric substrate by the enzymatic action.

This new method of enzyme detection opens new avenues of research to investigate mechanisms of enzyme action and to study the role that these enzymes play in many of the pathophysiological process in which they are involved. Some of these areas are:

(1) Single cell bioassay for proteinases.

Utilizing the immobilized fluorogenic substrates, single cells that produce specific proteinases can be identified and isolated.

If a cell grown on the collagen HEMA gel containing a fluorogenic substrate (with a spacer arm) produces the proteinase specific for the substrate, a greenish yellow fluorescence localized at this cell can be seen under the fluorescence microscope. Furthermore, by the use of a microscope spectrum analyzer, one can quantify the fluorescent product generated by proteinases released from a single cell. Cleavage of substrate at sites distant from the original source of secretion is expected to be minimal due to dilution by the medium. Thus, using this new method of single cell assay, the secretion of proteinases by individual cells at any period in their pathophysiological development can be studied by monitoring the localized concentration of the proteolytic product as a function of time.

(2) Detection of Intracellular Proteinases

Immobilized fluorogenic substrates also can be used to locate intracellular sites of proteinase synthesis and storage, particularly in phagocytic cells.

For this purpose, fluorogenic polyacrylamide beads of 1-2 microns in diameter prepared as outlined according to the invention may be employed. It has been demonstrated that particles of this size may be introduced intracellularly either by microinjection or by the natural process of engulfment (macrophage).

In addition, because of their small size, an important question that can be investigated is the temporal sequence of events occurring inside the cells that ultimately results in secretion of proteinase.

(3) Screening of Tissue Biopsies for Neoplasia

Another application is to localize specific sites of plasminogen activator activity in a tissue section and to use these sites as an indicator for neoplasia.

Slices taken from malignant tumors in mice and normal controls can be affixed to collagen-HEMA gels that have attached fluorogenic substrate. The underlying support can then be examined using epifluorescence, after various periods, for the appearance of generalized and site specific proteolytic activities. This method is believed to be applicable to the screening of tissue biopsies for neoplasia. Moreover, it is believed to provide a rapid, convenient means for examining the extent of metastasis in tissues.

(4) Study of Degradative Diseases

Uncontrolled destruction of intra or extra cellular proteins by proteinases is associated with pathological conditions, such as the breakdown of pulmonary elastin by elastase during emphysema, and tissue destruction during inflammation caused by proteinases released from polymorphonuclear leukocytes and mononuclear phagocytes. Also, macrophages that have been activated by various stimuli are able to modify their extracellular environment by secreting specific neutral proteinases such as plasminogen activator and elastase. Current knowledge about the role of proteinases in diseases has mainly been derived from tissues of heterogeneous populations of cells. Thus, the information obtained at the single-cell level, utilizing the immobilized fluorogenic substrate described in this invention is believed to provide means for understanding cell pathogenesis.

The development of this new methodology that can detect the production of proteinases from individual cells, allows the latter to be selected for cloning and permits investigation of factors that modulate proteinase secretion during pathophysiological conditions. The invention has application in molecular and cell biology as well as for diagnostic and therapeutic research in the fields of cancer, inflammation, and emphysema.

This invention will be described further in the following examples:

Materials

The following briefly describes measurement procedures employed in the examples:

Melting points were determined with a capillary melting point apparatus (Thomas-Hoover). Prior to submission of samples for elemental analyses, they were dried for 24 hr at 25° C (0.1 torr). Because these compounds are non volatile, fast atom bombardment mass spectrometry was used to confirm the molecular weights of the compounds. The fragmentation patterns shown by these compounds were consistent with their proposed Thin layer chromatography (TLC) was performed on Analtech silica gel plates containing a fluorescent indicator. Peptides containing 6 AQ or 1 alkyl-6-aminoquinoline ion appeared as blue fluorescent zones using long wavelength UV light (366 nm). The following solvent systems were employed for TLC elution: A. chloroformmethanol (9:1), B. chloroform/methanol (20:1), C. chloroform/methanol (7:1), D. chloroform/methanol (5:1), E. methanol, F. methanol/acetic acid (10:1). Ion exchange chromatography was conducted on Amberlite CG-50 resin (carboxylate form) using a stepwise gradient of ammonium carbonate from 0.1 to 1.0 M.

Fluorescence measurements were conducted with a Perkin-Elmer model MPF-44A recording fluorescence spectrophotometer that was standardized prior to each experiment such that a 6.$\mu$M solution of quinine sulfate in 0.1N $H_2SO_4$ produced a fluorescent intensity equal to 1.0 relative fluorescence unit (RFU).

Fluorescence microscopy and microfluorimetry were conducted with fluorescence microscope using a 100 watt mercury xenon lamp and a Leitz $I_2$ pre-excitation filter. Photographs were taken with a Leitz Orthomat-W automatic camera using Kodak Ektachrome ASA 400 film at 100 X magnification. Quantitative fluorescence microscopy was conducted using a microscope spectrum analyzer (MSA) (commerically available from Farrand Optical Co., Valhalla, N.Y.).

EXAMPLE I: SYNTHESIS OF PEPTIDYL AMINOQUINOLINE (6-AQ) AS FLUOROGENIC SUBSTRATES

A. Acylation of 6-aminoquinoline

Initially, simple peptides were constructed by acylation of 6-AQ with alanine, valine and arginine. These amino acids were chosen because it has been shown that proteinases such as elastase selectively hydrolyze substrates involving the carboxyl group of non aromatic, uncharged amino acids like L alanine and L valine. Trypsin-like proteinases cleave peptides after basic amino acids such as lysine and arginine.

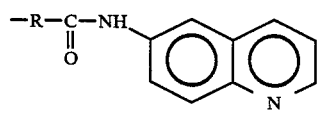

I  R = Cbz—Ala—

II  R = Cbz—Val—

III  R = Bz—L—Arg

6(N-Carbobenoxy-L-alanylamino)quinoline (I).

Into 15 ml of anhydrous tetradrofuran were added 3.03 mg (18.7 mmol) of carbobenzoxy L alanine. After stirring for 30 min at room temperature, 466 mg (3.23 mmol) of 6-aminoquinoline (prepared as described in Brynes, et al., supra, 1981) was added and the solution allowed to stir for 72 hrs. The product was isolated by diluting the organic solution with water, adjusting the pH to 10 with concentrated NaOH and extracting several times with chloroform. The combined organic phases were washed thoroughly with water, dried over $MgSO_4$, and evaporated under reduced pressure to afford a white solid. Recrystallization from acetone-petroleum ether produced 1.11 g, 98%yield of white needles, mp 171–172 ° C.; Rf(A)=0.62. Analysis calculated for $C_{20}H_{19}N_3O_3$:C, 68.77; H, 5.44; N, 14.25. Found: C, 69.05; H, 5.64; N, 11.94.

6-(N carbobenzoxy)-L-valylamino)quinoline (II)

Following the method described for compound I, compound II was prepared. Recrystallization from acetone-petroleum ether produced 69% yield, mp 180°–181° C., Rf(B)=0.56.

6-(N-Benzoyl-L-Arginylamino)guinoline (III)

The optically active arginine substrate was obtained as shown in scheme I:

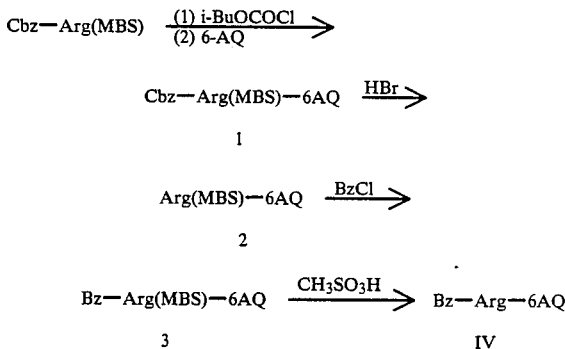

6-N-$\alpha$-Carbobenzoxy-N-$\omega$-p-methoxybenzenesulfonyl-L-arginyl-amino)quinoline To a solution of 800 mg (1.67 mmol) of N-carbobenzoxyL arginine and 184$\mu$l (1.67 mmol) of N methyl morpholine in 5 ml of dry dimethylformamide at −20° C. was added 211 $\mu$l (1.67 mmol) of isobutyl chloroformate. The resulting suspension was stirred at this temperature for 45 minutes an then 185 mg (1.28 mmol) of 6 AQ was added in 1 portion. The cooling bath was removed and the solution was then stirred for 24 hours at room temperature. The product was isolated by diluting the reaction solvent with 20 ml of water, adjusting the pH to 9 with 5% $NaHCO_3$, and extracting several times with ethyl acetate. The combined organic extracts were then dried over $MgSO_4$ and evaporated in vacuo to afford 798 mg of tan solids. Purification on preparative TLC plates (2000$\mu$m) by multiple elutions with solvent system B gave 605 mg (78% yield) of compound 1, mp 154°–155° C.; Rf(C)=0.51.

6-(N-p-Methoxybenzenesulfonyl L-arginylamino)-quinoline

To a solution of 300 mg (0.5 mmol) of 1 in 3 ml of glacial acetic acid was added 5 ml of 30% HBr in acetic acid was added 5 ml of 30% HBr in acetic acid. After 30 minutes, the solution was diluted with 100 ml of anhydrous diethyl ether, which resulted in the precipitation of product as white flocculent crystals. These were washed several times by decantation from diethyl ether and dried overnight in vacuo. Attempts to purify the dihydrobromide salt of 2 were not successful owing to its deliquescence. Therefore, it was used directly in the following reaction.

6-(N-α-Benzoyl-Nω-methoxybenzenesulfonyl-L-arginyl-amino) quinoline

Dihydrobromide salt 2 (216 mg., 0.36 mmol) was added to a solution of tetrahydrofuran: water (9:1) and cooled to 5° C. Triethylamine (205μl, 1.48 :mmol) and benzoyl chloride (46 μl, 0.40 mmol) were added sequentially and the solution was stirred for periods of 1 hour each at −5, 0, and 25° C. The product was isolated by removing the solvent in vacuo, dissolving the residue in 1 ml of ethanol, and precipitating the benzoylated product by the addition of diethyl ether. Preparative TLC using solvent system B gave 176 mg (85% yield) of compound 3, mp 167° C. decomposes; Rf(D)=0.59.

6-(N-Benzoyl-L-arginylamino)quinoline(IV)

To 33 mg (0.06 mmol) of compound 3 was added 850μl of methane sulfonic acid containing 15 μl of anisole. After stirring at room temperature for 40 minutes, the product was precipitated by the addition of 50 ml of diethyl ether, washed several times by decantation from this solvent, and dried under high vacuum. The crude product was then purified by passage through an ion-exchange column (carboxylate form) (commercially available as Amberlite CG-50 from Sigma Chemical Co., St. Louis, Mo.) using a discontinuous gradient of ammonium carbonate (0.1–1.0 M). The blue fluorescent fractions were combined and lyophilized to afford 18.5 mg (71% yield) of compound IV as its bicarbonate salt, mp 135°–140° C. decomposes. The product gave a positive Sakaguchi test and migrated as a single spot in several TLC solvents. Rf(F)=0.41, [a]D=+4.0° (c=1 ml, methanol). Analysis calculated for $C_{22}H_{24}N_6O_2 \cdot H_2CO_3 \cdot 2H_2O$: C, 54.97; H, 5.82; N, 14 16.72. Found: C, 54.66; H, 5.38; N, 16.98.

B. Preparation of Oligopeptidyl Fluorogenic Substrates 6-(N-Carbobenzoxy-L-alanyl-L-alanyl-L-alanylamino) quino-line (V)

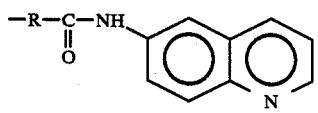

V.   Cbz—Ala—Ala—Ala

VI.  Suc—Ala—Ala—Ala0

VII. Cbz—Ala—Ala—

VIII. Cbz—Ala—Ala—Pro—Val—

IX.  Bz—Val—Gly—Arg—

(V) Shown below is the scheme for the synthesis of Cbz-Ala-Ala-Ala-6AQ. Scheme II.

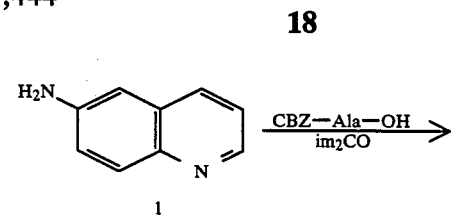

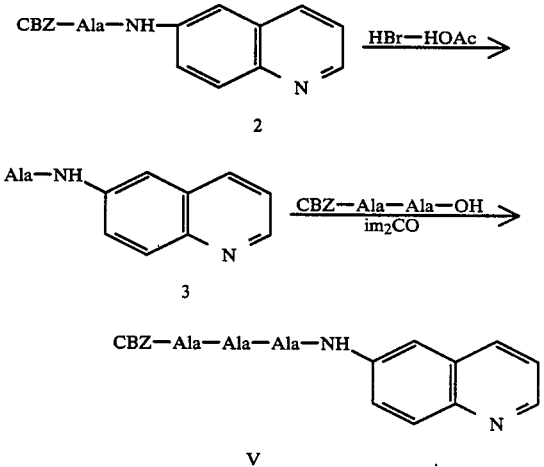

To a solution of 230 mg (0.66 mmol) of 2 in 2 ml of glacial acetic acid was added 5 ml of 30% HBr in acetic acid. After 30 minutes at room temperature, the solution was diluted with 50 ml of anhydrous ether, which precipitated compound 3 as its dihydrobromide salt in the form of a fine white powder. These solids were washed several times with ether, dried overnight in vacuo, and used in the following reaction without further purification. To 1.0 g (3.4 mmol) of carbobenzoxy-L-alanyl-L-alanine in 15 ml of anhydrous tetrahydrofuran at room temperature was added 551 mg (3.4 mmol) of 1,1'-carbonylidiimidazole. After 30 minutes, the dihydrobromide salt of 3 (250 mg, 0.66 mmol) was added to the solution together with 2 equivalents of triethylamine to ensure the formation in situ of its free base. The solution was then stirred for 72 h at room temperature and the crude product that had precipitated was isolated by filtration. Recrystallization from methanol afforded 111 mg which represents a 35% overall yield from 2; mp 263°–265° C; Rf(A)=0.50. Analysis calculated for $C_{26}H_{29}N_5O_5$; C, 63.45 H, 5.90; N, 14.25. Found: C, 63.06; B, 5.90; N, 14.25.

6-[N-(Succinylamido)-L-alanyl-L-alanyl-L-alanylamino]-quinoline (VI)

To a solution of 111 mg (0.226 mmol) of V in 1 ml of glacial acetic acid was added 3 ml of 30% HBr in acetic acid. After 30 minutes, the solution was diluted with 50 ml of ether, which resulted in the precipitation of white crystals. The solids were filtered, washed thoroughly with ether, and dried overnight under vacuum to produce a deliquescent dihydrobromide salt. This was dissolved in 5 ml of methylene chloride containing 2.2 equivalents of triethylamine. Succinic anhydride (22 mg, 0.216 mmol) was added and the solution allowed to stand overnight at room temperature. At the end of this time, the white precipitate that had formed was collected and recrystallized from methanol to afford 88 mg (97% yield); mp 193°–194.5° C.; Rf(A)=0.28. Analysis calculated for $C_{22}H_{27}N_5O_6 \cdot H_2O$; C, 57.77; H, 591; N, 15.32. Found: C, 58.32; H, 5.87; N, 13.90. Fast atom bombardment mass spectrum of this compound: calculated MW (458)+OAc- . Found: 458(M+).

6-(N-Carbobenzoxy-L-alanyl-L-alanylamino)quinoline (VII)

This dialanyl peptide was prepared and isolated by using conditions similar to that described above for the synthesis of 2. From 1.0 g (3.43 mmol) of carbobenzoxy-L-alanyl-L-alanine, 551 mg (3.43 mmol) of 1,1'-carbonyl diimidazole, and 82 mg (0.57 mmol) of 1 was prepared 177 mg of crude product. Recrystallization from acetone-petroleum ether afforded 167 mg (70% yield): mp 223-225° C.; Rf(A)=0.52. Analysis calculated for $C_{23}H_{24}N_4O_4$: C, 65.71; H, 5.71; N, 13.30. Found: C, 65.58; H, 5.83; N, 13.14.

Shown below is the scheme (III) for the synthesis of 6-(N-Carbobenzoxy-L-alanyl-L-alanyl L-piolyl-L-valylamio) quinoline (VIII).

alanyl-L-proline and 107µl (0.98 mmol) of N-methylmorpholine in 4 ml of anhydrous dimethylformamide at −15° C. was added 128µl (0.98 mmol) of isobutyl chloroformate. The reaction mixture was stirred at this temperature for 45 minutes to complete the formation of the mixed anhydride. To the dihydrobromide salt of 3 (360 mg, 0.89 mmol) in 2 ml of anhydrous dimethylformamide, was added 195 µl (1.78 mmol) of N-methylmorpholine. This solution was then added to the mixed anhydride reaction mixture at −15° C. The cooling bath was then removed and the solution was stirred for 24 hours at room temperature. The produced was isolated by diluting the reaction solvent with a saturated solution of $NaHCO_3$ (50 ml) and extracting with ethyl acetate (2×25 ml). The organic layer was washed with water (3×25 ml), saturated NaCl solution (1×25 ml), dried over $MgSO_4$, and evaporated in vacuo to afford 200 mg

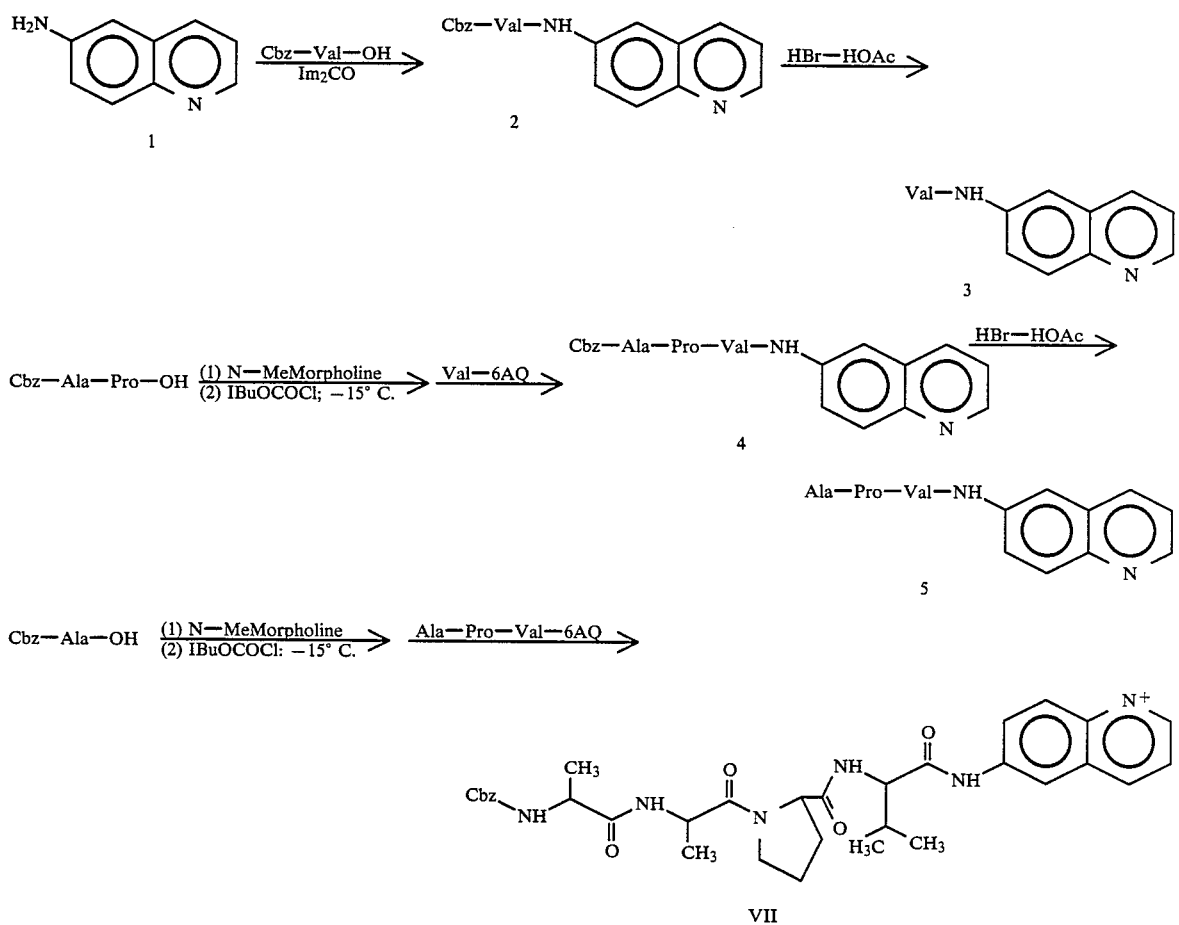

6-(N-Carbobenzoxy-L-valylamino(quinoline)

The acylation of 6-AQ by valine was performed as previously described.

6-(N-Carbobenzoxy-L-alanyl-L-prolyl-L-valylamino) quinoline

To a solution of 50 mg (0.132 mmol) of 2 in 1 ml of glacial acetic acid was added 2 ml of 30% HBr in acetic acid. After 45 minutes at room temperature, the solution was diluted with 50 ml of anhydrous ether, which precipitated compound 3 as its dihydrobromide salt (white flocculent). This precipitate was washed several times with ether, dried under reduced pressure, and used in the following reaction without further purification. To a solution of 313 mg (0.98 mmol) of carbobenzoxy-L- of a thick liquid (41% yield). Crystallization was unsuccessful. Rf(B)=0.39. High resolution mass spectrometry: M+ calculated: 545.26373; found: 545.2608.

6-(N-Carbobenzoxy-L-alanyl-L-alanyl-L-prolyl-L-valylamino) quinoline (VIII)

To a solution of 550 mg (1.01 mmol) of 4 in 1 ml of glacial acetic acid was added 2 ml of 30% NGr in acetic acid. After 45 minutes at room temperature, the solution was diluted with anhydrous ether forming a white precipitate of the dihydrobromide salt 5. The product was washed with ether several times and dried under pressure. 5 was directly used in the next step without further purification. To a solution of 225 mg (1.01 mmol) of carbobenzoxy L-alanine and 111μl (1.01 mmol) of N-methylmorpholine is 4 ml of anhydrous dimethylformamide at −15° C. was added 131 μl (1.01 mmol) of isobutyl chloroformate. After 45 minutes, the dihydrobromide salt of 5 (526 mg, 0.918 mmol) was added to the solution together with 2.5 equivalents of N-methylmorpholine to ensure formation in situ of its free base. The solution was then stirred for 24 hours at room temperature and the product isolated by diluting the organic solvent with water, adjusting the pH to 9.0 with 5% NaHCO$_3$, and extracting with ethyl acetate. The extracts were dried (MgSO$_4$), and the solvent was removed in vacuo. Recrystallization from acetone petroleum ether afforded 426 mg (75% yield): mp 194°-196° C.; Rf(B)=0.20. Analysis calculated for C$_{33}$H$_{40}$N$_6$O$_6$: C, 64.27; H, 6.54; N, 13,63. Found: C, 64.19; H, 6.93; N, 13.14.

Shown below is the scheme (IV) for the synthesis of 6-(N-benzoyl-L-valyl-glycyl-L-arginylamino)quinoline (IX)

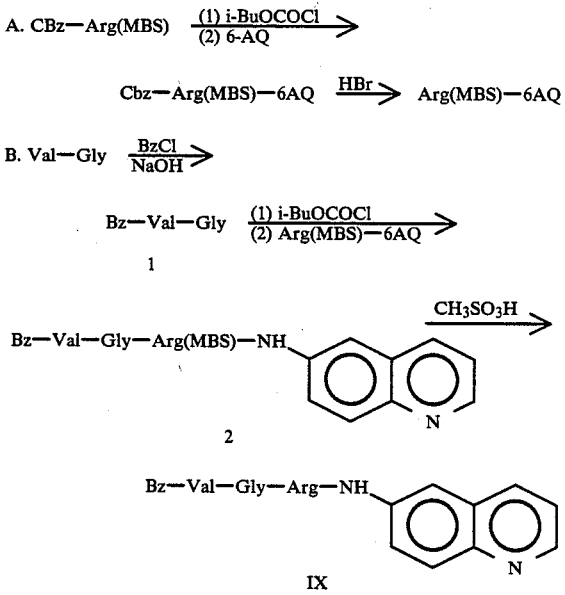

Benzoyl-L-valyl-glycine

To a solution of L-valyl-glycine (1.0 g. 5.74 mmol) in 1 N NaOH (4.74 ml, 5.74 mmol) cooled to −5° C., 6.89 ml (689 mmol) of 1N NaOH and 968 1 (6.89 mmol) of benzoyl chloride were alternately stirred in for 30 minutes. After 90 minutes, the reaction mixture was diluted with water and washed with diethyl ether. The product was isolated by precipitation in the aqueous layer which was acidified to pH 1.5. The precipitate was then washed with diluted HCl, water, and ether. Recrystallization from water afforded 1.16 g (73% overall yield from 1): mp 190°-191° C.; Rf(D)=0.2.

6-N-benzoyl-L-valyl-glycyl-N-[(p-methoxybenzyl)-sulfonyl]L-arginylamino quinoline Into 3 ml of anhydrous dimethylformamide at −20° C. were dissolved 235 mg (0.843 mmol) of 1 and 93 μl (0.843 mmol) of N-methylmorpholine. After 5 minutes, 109 μl (0.843 mmol) of isobutyl chloroformate was added, the resulting suspension was stirred at this temperature for 45 minutes, whereupon 6-(N-p-methoxybenzenesulfonyl-L-arginylamino)quinoline. (471 mg, 0.702 mmol) was introduced into the reaction mixture, and the reactants were gradually allowed to reach room temperature. After 12 hours, the product was isolated by evaporating the dimethylformamide in vacuo, dissolving the residue in ethyl acetate (some of which does not go into solution), diluting the organic solvent with water, and adjusting the pH to 9.0 with 5% NaHCO$_3$. Extraction with ethyl acetate, dissolving in methanol the residue left behind after ethylacetate, and evaporation of the solvents under reduced pressure gave 495 mg of crude 2. The product was purified by preparative scale TLC using multiple elutions in solvent system A to afford 395 mg (71% yield): mp 144°-146° C.; Rf(D)=0.61. The Fast atom bombardment mass spectrum of this compound: C$_{36}$H$_{42}$N$_8$O$_7$S: (731)+. Found: (M+H)+. Analysis calculated for C$_{36}$H$_{42}$O$_7$S: C, 59.16; H, 5.79; N, 15.33. Found: C, 59.11; H, 5.75; N, 15.21.

6-(N-Benzoyl-L-valyl-glycyl-L-arginylamino) quinoline (IX)

To 109 mg (0.149 mmol) of 2 was added 745 μl of methane sulfonic acid containing 37 μ1 of anisole. After continuous stirring at room temperature for 40 minutes, the product was precipitated with the addition of diethyl ether; washed several times by decantation from the solvent and dried in vacuo. The crude product was dissolved in 10 ml of water and passed through an ion-exchange column (Amberlite, CG-50 resin, carboxylate form). The product was eluted from the column by a stepwise gradient of ammonium carbonate from 0.05 to 0.3 M. The blue fluorescent fractions were combined and lyophilized to produce 52 mg (56% yield): mp 167°-169° C.; Rf=0.29 (n-butanol: acetic acid: water, 3:1:1); positive Sakaguchi test Fast atom bombardment mass spectrum of IX: calculated for MW (561)+. Found: 561 (M+).

C. Quaternization of Peptidyl Aminoquinolines

As mentioned before, the ring nitrogen of 6-aminoquinoline can be readily quaternized by alkylating agents. In this way, fluorogenic substrates containing 6-AQ could be immobilized to a solid support. Quaternized or charged substrates are better models of the immobilized compounds than their uncharged counterparts. Consequently, substrates with the charged fluorogenic cations 1-methyl-6-aminoquinolinium (MAQ+) and 1-allyl- 6-aminoquinolinium (AllylAQ+) as the leaving groups were synthesized.

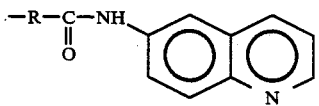

X.   R$_1$: Cbz—Phe—, R$_2$: CH$_3$—

XI.  R$_1$: Cbz—Ala—Ala—, R$_2$: CH$_3$—

XII. R$_1$: Cbz—Ala—Ala—Ala—, R$_2$: CH$_3$—

XIII. R$_1$: Cbz—Ala—Ala—Pro—Val—, R$_2$: CH$_3$—

XIV. R$_1$: Cbz—DL—Arg—, R$_2$: CH$_3$—

XV.  R$_1$: Cbz—DL—Arg—, R$_2$: CH$_2$=ChCh$_2$—

XVI. R$_1$: Cbz—Phe—, R$_2$: CH$_2$=ChCh$_2$—

1-Methyl-6-(N-carbobenzoxy-L-phenylalanylamino) uinolium Iodide (X)

To 2 ml of methyl iodide was added 20 mg (0.047 mmol) of 6-(N-carbobenzoxy-L-phenylalanylamino)- quinoline (Brynes et al., 1981). After stirring at room temperature for 24 hours, the two-phase suspension was evaporated to dryness under reduced pressure and recrystallized from ethanol-ether to afford 25 mg (95% yield): mp 141° C. decomposes; Rf(E)=0.07. Analysis calculated for $C_{27}H_{26}N_3O_3I.H_2$): C, 57.15; H, 4.62; N, 7.40. Found: C, 55.25; H, 4.95; N, 7.17. Fast atom bombardment mass spectrum of this compound: calculated for MW (440)+I−. Found: 440(M+).

1-Methyl-6-(N-carbobenzoxy-L-alanyl-L-alanylamino) quinoline Iodide (XI)

To 29 mg (0.06 mmol) of VII in 5 ml of chloroform was added 1 ml of methyliodide. After the mixture was stirred for 24 hours at room temperature, the solvent and alkylating agent were removed in vacuo to afford a thick orange oil. Crystallization from ethanol-ether produced 36 mg (90% yield), of a finely divided yellow powder: mp 135° C. decomposes; Rf(E)=0.06. Analysis calculated for $C_{24}H_{27}N_4O_4I$: C, 51.26; H, 4.84; N, 9.96. Found: C, 50.05; H, 5.23; N, 9.85. Fast atom bombardment mass spectrum: calculated for MW (435)+I−. Found: 435 (M+).

1-Methyl-6 -(N-carbobenzoxy-L-alanyl-L-alanylamino) quinoline Iodide (XII)

To 93 mg (0.19 mmol) of V in 5 ml of anhydrous dimethylformamide was added 1 ml of methyl iodide. After the mixture was stirred at room temperature in the dark for 24 hours, the solvent and alkylating agent were removed under reduced pressure to afford a thick orange oil. This was dissolved in a minimal volume of ethanol and precipitated as a solid by the dropwise addition of ether. After filtration, the product was washed several times with anhydrous ether and recrystallized from ethanol-ether to give 75 mg (61% yield): mp 132° C. decomposes; Rf(E)=0.06. Analysis calculated for $C_{27}H_{32}N_5O_5I$: C, 51.08; H, 5.09; N, 11.06. Found: C, 48.31; H, 4.80; N, 10.26. Fast atom bombardment mass spectrum: calculated for MW(506)+$I^{31}$. Found 506 (M+).

1-Methyl-6-N-carbobenzoxy-L-analyl-L-analyl-L-prolyl -L-valylamino)quinoline Iodide (XIII).

To 100 mg (0.162 mmol) of VIII in 5 ml of anhydrous dimethylformamide was added 1 ml of methyl iodide. After the mixture was stirred at room temperature for 48 hr, the solvent and alkylating agent were removed under reduced pressure to afford a thick orange oil. This oily material was dissolved in ethanol and precipitated with dropwise addition of ether. Precipitate was washed several times with ether and finally recrystallized from ethanol ether to give 74 mg (60% yield): mp 45° C. decomposes; Rf(F)=0.10. Fast atom bombardment mass spectrum: calculate for MW (631)+I− Found 631 (M+).

1-Methyl-6-(N-benzoyl-DL-arginylamino)-guinolinium Diiodide (XIV)

A solution consisting of 25 mg (0.05 mmol) of III, 2 ml of methyl iodide, and 0.5 ml of dimethylformamide was allowed to stand at room temperature in the dark for 48 hr The solvents were removed under reduced pressure and ether was added to solidify the oily residue. Recrystallization from ethanol-ether produced 22 mg (62% yield): mp 220° C. decomposes; Rf(E)=0.06; positive Sakaguchi test. Analysis calculated for $C_{23}H_{28}N_6O_2I_2$: C, 40.97; H, 4.18; N, 12.47. Found C, 40.60; H, 4.64; N, 11.79.

1-Allyl-6-(N-benzoyl-DL-arginylamino)quinoline Dibromide (XV)

This substrate was prepared and isolated by using conditions similar to that described above for the synthesis of XIV. From 32 mg (0.069 mmol) of III and 60 μl of allyl bromide in 1.0 ml of dimethylformamide, was prepared 34 mg of product (81% yield): mp 60° C. decomposes; Rf(F)=0.16; positive Sakaguchi test Analysis calculated for $C_{25}H_{30}N_6O_2Br_2$: C, 49.52; H, 4.99; N, 13.86. Found: C, 48.99; H, 4.58; N, 13.41.

1-Allyl-6-(N-carbobenzoxy-L-phenylalanylamino) quinoline Bromide (XVI)

A solution consisting of 100 mg (0.235 mmol) of 6-(N-carbobenzoxy-L-phenylalanylamino)quinoline (Brynes, et al., 1981), 204 1 of allyl bromide, and 0.5 ml of dimethylformamide was allowed to react at room temperature for 48 h and at 50° C. for 12 h. Crude product was isolated by precipitation with ether followed by two ether washes. The compound was purified by dissolving the solid in water at 50° C., filtering the undissolved material and lyophilizing to obtain pure XVI. Recrystallization from ethanol/ethyl acetate yielded 50 mg (39% yield): mp 160° C. decomposes, 219° C. melts;Rf(E)=0.08. Fast atom bombardment mass spectrum of XVI: calculated for MW (466)+Br−. Found 466 (M=).

The fluorescense spectra of the substrates and respective fluorophores were measured by exciting at the wavelength of maximum emission and scanning from 200 nm to 400 nm. Emission spectra were obtained by emitting at wavelength of the maximum excitation and scanning from 400 nm to 700 nm. The spectra were all uncorrected.

Effects of pH on the spectroscopic characteristics of 6-AQ were determined by obtaining the fluorescence spectra of the amine fluorophor from pH 2.0 to pH 9.0.

The fluorescence spectra of Cbz-Ala Ala-Ala-MAQ+demonstrates that lengthening the peptide chain does not interfere with desirable spectroscopic properties demonstrated. The spectroscopic properties of the fluorophores enable their appearance to be monitored during the assay at wavelengths where they are most fluorescent. Even in the presence of an excess amount of substrate, these fluorophores can be measured without high levels of background emission that limit the sensitivity of detection.

D. COVALENT ATTACHMENT OF PEPTIDYL-6AQ TO A SOLID SUPPORT

1. Preparation of Fluorogenic Polyacrylamide Microspheres

The preparation of covalently immobilized, fluorogenic substrates for elastase and chymotrypsin is outlined in Scheme V.

1 —$CONH_2$

Polyacrylamide Microspheres

↓ Ethylene Diamine

-continued

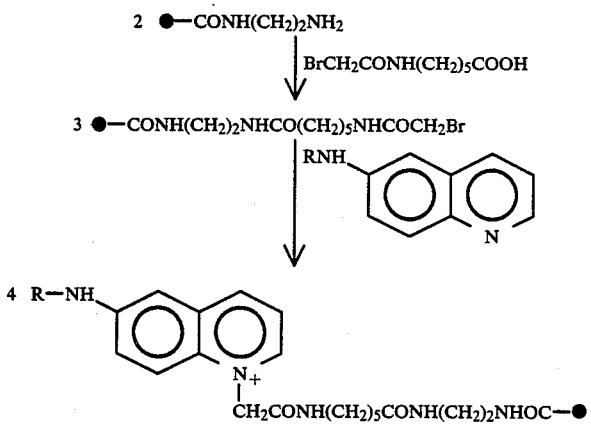

Polyacrylamide microspheres 1 (commercially available as Bio-Gel P-10 ™ from Bio-Rad Chemical Divison, Richmond, Cal) were transamidated at 90° C. for 24 hr in anhydrous ethylene diamine to form the N-(2-aminoethyl) polymer 2. Isolation and final washing were done as described by the method of Inman, *Methods in Enzymology* (Academic Press, N.Y., N Y. 1974), pp. 30–58. The poly(2-aminoethyl)acrylamide derivative generated in step 1 was acrylated with 6-(α-bromoacetamido) hexanoic acid (BACA) (prepared as described by Inman, supra, 1974) to yield microspheres having a long spacer arm that terminates in a good alkylating group 3. The bromoacetamidocaproyl aminoethyl derivative 3 was obtained by a mixed anhydride formed from BACA (800 mg., 3.15 mmol) and isobutyl chloroformate (0.431 ml. 3.15 mmol). The reaction mixture was then added directly to the aminoethyl gel suspension 2 (8.0 ml of bed volume or 2.0 g of dry microspheres). The reaction was run for a period of 12 h. Isolation of 3 was done as described by Inman (1974). Samples were tested for free amino groups with Trinitrobenzenesulfonic acid (TNBS) in borate solution. Acetic anhydride was added until the results of the TNBS reaction were negative.

The reactive microspheres 3 (2 ml bed volume or 0.22 g of dry weight) were used to guaternize the ring nitrogen of the quinoline fluorophore of soluble substrates. The tripeptidyl elastase substrate Cbz-Ala-Ala-Ala-6AQ (200 mg. 0.41 mmol) was quaternized in anhydrous dimethylformamide at room temperature for 72 hr. The extended time required to complete the substitution of bromine was typical of a two-phase reaction. At the end of the reaction time, unreacted substrate that was not attached to the solid phase was isolated quantitatively by filtration and recovered by precipitation with water. The recovered tripeptidyl elastase substrate served as a measure of the amount of substrate incorporated into the microspheres (1.2 mmol of substrate/g of dry microsphere). Microspheres were stored in anhydrous dimethylformamide at 4° C. and prior to use were resuspended several times in a large volume of 0.2 M NaCl to free them from organic solvent.

EXAMPLE IA

Example I is repeated except that the fluorogenic moiety employed is 3-aminoquinoline.

EXAMPLE IB

Example I is repeated except that the flurogenic moiety employed is 4 dimethylaminomethyl- 6-aminocoumarin (DAC) Quaternization of the dimethylaminomethyl group of the 6-(oligopeptidyl) coumarin derivative, by the alkylating end of the spacer-polymer complex requires approximately the same time as in Example I.

EXAMPLE IC

Example IB is repeated except that 2-dimethylaminomethyl-6-aminonaphthalene (DAN) is used in place of DAC.

EXAMPLE II:

The following immobilized substrates can be prepared according to the process described in Example I:

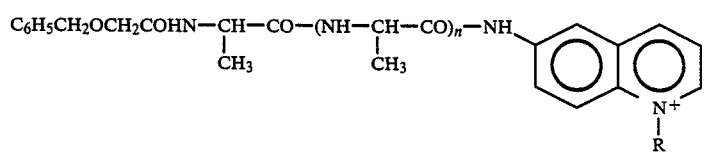

(A) n = 1 or 2; R = $CH_2CONH(CH_2)_5CONHCH_2CH_2NHCO$—polyacrylamide (B) n = 1 or 2; R = $CH_2CONHCH_2CH_2NHCO$—polyacrylamide (C) n = 1 or 2; R = $CH_2COHN$—polystyrene (D) n = 1 or 2; R = $CH_2CONHCH_2CH_2CH_2$—silica gel

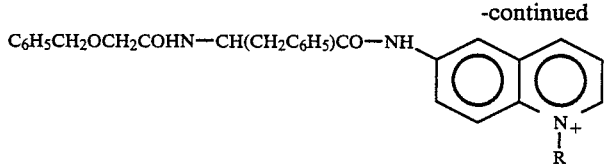

(E) R = CH$_2$CONH(CH$_2$)$_5$CONHCH$_2$CH$_2$NHCO—polyacrylamide (F) R = CH$_2$CONHCN$_2$CH$_2$NHCO—polyacrylamide (G) R = CH$_2$CONH—polystyrene (H) R = CH$_2$CONHCH$_2$CH$_2$CH$_2$—silica gel

EXAMPLE III: COPOLYMERIZATION OF THE FLUOROGENIC SUBSTRATE WITH 2-HYDROXYETHYL METHACRYLATE (HEMA).

Preparation of 2-Hydroxyethyl Methacrylate (HEMA) Gels

1-Allyl-6-(N-carbobenzoxy-L-alaynyl-L-alanyl-L-alanylami no)-guinolinium bromide (I). A solution consisting of 50 mg. (0.102 mmol) of Cbz-Ala-Ala-6AQ, 100μl of allyl bromide and 1.0 ml of anhydrous dimethylformamide was allowed to react at room temperature in the dark for 48 h. The solvents were removed in vacuo and ether was added to solidify the oily residue. The solids were dissolved in water, filtered, and lyophilized to yield 56 mg. (90% yield): mp 119° C. decompoes; Rf=0.06 in methanol. Fast atom bombardment mass spectrum: calculated for MW (532)+Br⁻.

The procedure outlined below was used to prepare collagen-HEMA gels containing the particular fluorogenic substrate: 1 ml of HEMA, 1 ml of ethylene glycol, 1 ml of calf skin collagen solution (2 mg/ml), the fluorgenic substrate in 0.05 M Tris-Cl (pH 7.4) buffer containing 0.15 M NaCl, 0.1 ml of 6% (w/v) ammonium persulfate, and 0.1 ml of 12% (w/v) sodium metabisulfite are added in sequence while in ice. After mixing, the gels are polymerized at room temperature between two glass microscope slides separated by coverslips. The approximate thickness of the gel is 0.5 mm. The resulting clear HEMA gels are dialyzed exhaustively against the Tris-Cl buffer to remove residual monomer and ethylene glycol. The HEMA gels were then cut into 1.4 cm diameter disks with each gel disk containing approximately 48μg. of collagen and a final concentration of 5 mM of the fluorogenic substrate.

A 12-atom spacer group was linked to the substrate to increase the length of the arm that separates the substrate from the gel matrix (Scheme VI).

Scheme VI

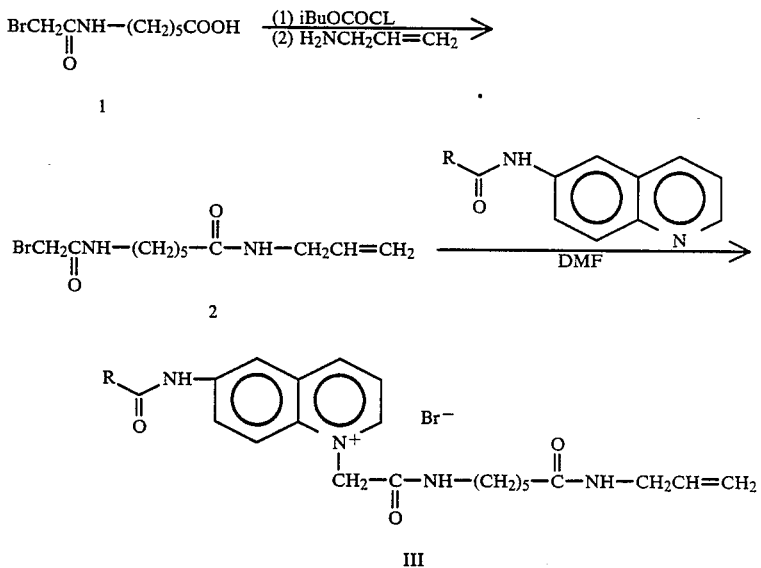

Bromoacetamido caproyl allylamide. To a solution of 1.156 g (4.58 mmol) of 1 and 503 μl (4.58 mmol) of N-methylmorpholine in 15 ml of anhydrous tetrahydrofuran at 0° C. was added 600μl (4.58 mmol) of isobutyl chloroformate. The resulting suspension was stirred at this temperature for 45 mins. and then 310 μl (4.17 mmol) of allyl amine was added slowly. The reaction mixture was stirred at 0° C. for 2 hrs. and at room temperature for another 2 hrs. The product was isolated by filtering away the N-methyl morpholinium hydrochloride salt formed, diluting the filtrate with water, adjusting the pH to 9 with 5% NaHCO$_3$ and extracting several times with ethyl acetate. The combined organic extracts were dried over MgSO$_4$ and the solvent was evaporated under reduced pressure to yield 417 mg of 2 (34% yield): mp 94°–96.5° C.; RF=0.11 in chloroform/methanol, 9:1.

1-Acetylamido caproic allyl amide -6-(N-carbobenzoxy-L-valanyl-L-analyl-L-alanylamino)quinoline bromide (III).

To 101 mg (0.20 mmol) of Cbz-Ala-Ala-Ala-6AQ in 5 ml of anhydrous dimethylformamide was added 178 mg (0.61 mmol) of 2. The solution was stirred for 24 hours at room temperature in the dark. The dimethylformamide was then evaporated under reduced pressure. The crude product was dissolved in 50 ml of water and passed through an ion-exchange column (Amberlite, cg-50 resin, carboxylate form). The product was eluted from the column by a stepwise gradient of ammonium carbonate from 0.05 to 0.2 M. The blue fluorescent fractions were combined and lyophilized to produce 73 mg (52% yield): mp 210° C. decomposes; Rf=0.28 in methanol/acetic acid, 20:1. Fast atom bombardment mass spectrum: calculated for MW (702)+Br−.

Preparation of Fluorogenic HEMA Gels with a Spacer Arm.

The fluorogenic substrate III was copolymerized with 2-hydroxyethylmethacrylate as described above to form a three dimensional network.

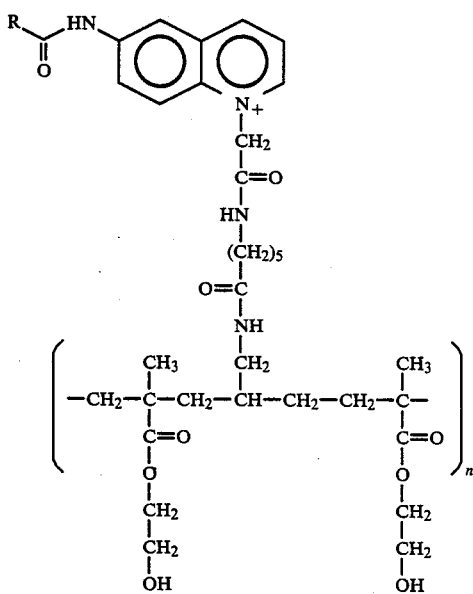

where n represents an integer greater than 2 and sufficiently large so that the polymer formed was a gel.

Example IV: ENZYMATIC HYDROLYSIS:

This new assay measures proteolytic activity utilizing immobilized fluorogenic substrates in which the fluorogenic moiety is covalently attached to an insoluble support. Because the chromophore (6-aminoquinoline) remains bonded to the support after proteolysis, it cannot diffuse from the site of cleavage.

A. With Substrates Immobilized to Polyacrylamide Microspheres.

Cbz-Ala-Ala-Ala-6AQ was shown to be a good soluble substrate for elastase. The specific activities of porcine pancreatic elastase (2 x crystallized) enzyme were determined using orcein elastin (Sacher et al., 90 *Proc. Soc. Exp. Biol. Med.* 323 (1955). Pancreatic elastase activity was measured in 67 mM Tris-HCl buffer, pH 8.8, using microspheres that had been alkylated with Cbz-Ala-Ala-Ala-6AQ. Samples of microspheres were exposed to elastase (0.07 mM), or buffer alone at 37° C.

After various periods of incubation, the microspheres were removed for examination with the fluorescence microscope. See FIG. 1 which is a graph of time (hrs.) v. fluorescence (RFU).)

Fluorescence microscopy and microfluorimetry were conducted using an epifluorescence microscope. At each time point, 10 microspheres were selected at random in both the control and enzyme-treated samples of their emissions measured. The correlation coefficient for a double-reciprocal plot of the increase in fluorescence intensity versus time for microspheres exposed to elastase or chymotrypsin was 0.99.

B. With HEMA Gels Copolymerized with the Fluorogenic Substrate

Gels of 1.4 cm in diameter and approximately 0.5 mm thickness were prepared according to the procedure set forth in Example III with different amounts of the substrate: 4.0, 3.0, and 2.0 mM respectively.

After various periods of incubation at 37° C. the gels were removed for examination with the fluorescence microscope.

Figure 2:
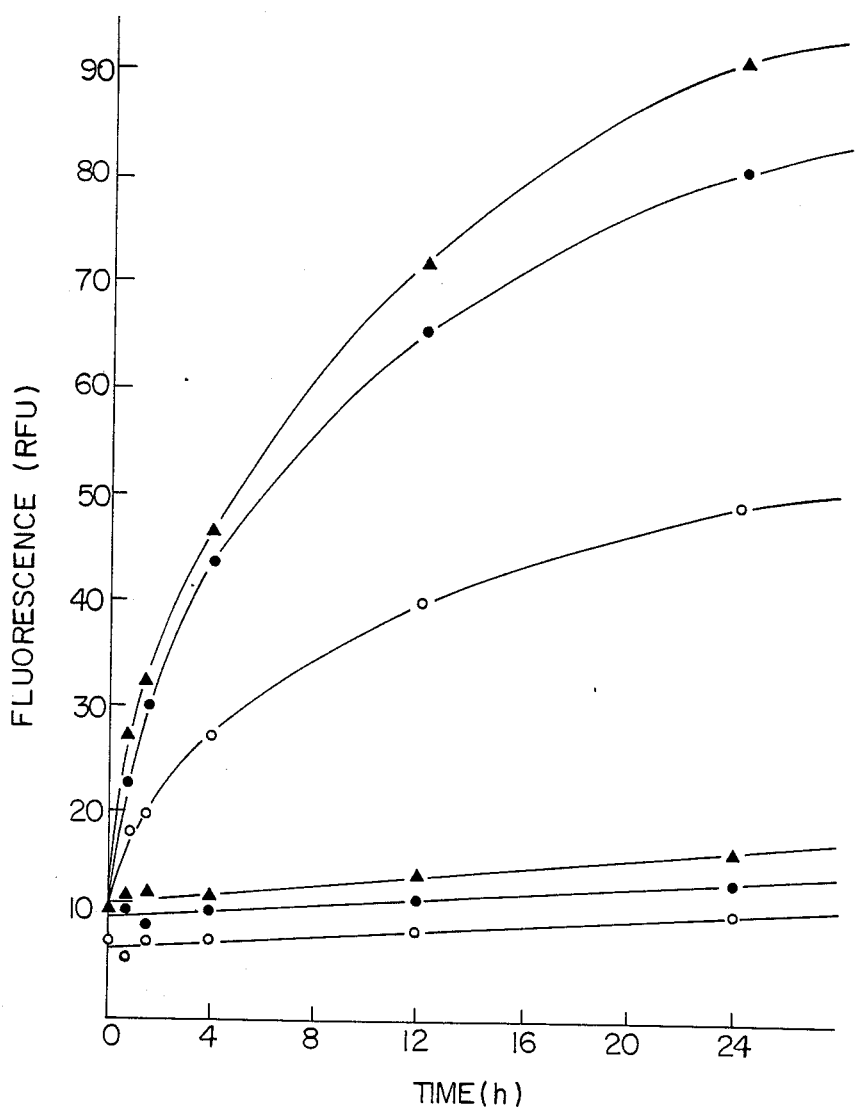

Fluorescence microscopy of the gels was performed by removing them from the wells to measure their emission at different points in time. Fluorescence was determined at the center of the gels from both controls and enzyme treated samples. The correlation coefficient for a double reciprocal plot of the increase in fluorescence intensity of each gel exposed to chymotrypsin versus time was 0.99. (See FIG. 2 which is a graph of time (hrs.) vs. fluorescence (RFU).)

These experiments clearly demonstrate the feasibility of using immobilized fluorogenic substrates to detect proteinases in vitro. These substrates proved to be effective indicators of proteolytic cleavage and can be utilized for localization and quantitation of proteinase action. The choice of sequence of the amino acids linked to the fluorophore determines the specificity of the synthetic substrate to a given proteinase. This new method of detection and quantitation of proteolytic activity permits the investigation of the roles that proteinases play in physiological and pathological conditions.

EXAMPLE V: CELL ADHESION AND GROWTH

A. Preparation of the Solid Supports for Growth Studies.

Polyacrylamide microspheres, derivatized with fluorogenic substrates prepared according to the procedure set forth in Example I, were swollen and extensively washed in phosphate buffered saline that was $Ca^{2+}$ and $Mg^{2+}$ free (PBS-CMF). Microspheres were then sterilized by resuspending two times in 70% (V/V) ethanol in distilled water. The ethanol solution was removed, and the microspheres was rinsed three times in sterile PBS CMF and once in culture medium before use.

The fluorogenic HEMA gels, prepared according to the procedures of Example III, were cut in disks of 1.4 cm in diameter, and sterilized in $Ca^{2+}$, $Mg^{2+}$ free Puck's Saline Solution, which contains 100 units/ml penicillin and 100 g/ml streptomycin , by placing them for 2 hours under ultraviolet light. The gels then were transferred to fresh Puck's Saline Solution with antibiotics and stored at 4° C. prior to use for cell culture studies.

B. Cell Cultures

1. Cell Culture on Polyacrylamide Microspheres with the Immobilized Fluorogenic Substrate.

Human embryonic lung fibroblasts (IMR-90) were used in 11th passage. Cells were seeded at $4.0 \times 10^6$ cells in 25 ml of Dulbecco's Modified Eagle's Medium (DMEM) supplemented with 10% fetal bovine serum in a siliconized spinner vessel containing 1.0 ml of hydrated microspheres derivatized with the fluorogenic substrate Cbz-Ala-Ala-Ala-6AQ (1.2 mmol of substrate/g dry microspheres). Spinner vessels were stirred 2 min every 60 min for 3 hours. IMR-90 and microspheres were then allowed to incubate overnight at 37° C. in a humidified atmosphere of 5% $CO_2$/95% air. After 24 hours of incubation aliquots of microspheres were removed and placed in sterile petri dishes containing 5 ml of DMEM for microscopic observation. Cells on microspheres were photographed with a Leitz phase-contrast microscope using a Vario-Orthomat automatic camera; and 667 black and white Polaroid film, 3,000 ASA at 160 X magnification.

Human monocytes were isolated from fresh blood using Ficoll-Pague density gradients (Wright et al., 156 J. Exp. Med. 149-1164 (1982)) and further purified by a continuous Percoll gradient. Monocytes were cultured in Eagle's minimal essential medium (MEM) supplemented with glutamine (2.0 mM) and non-essential aminoacids (0.1 mM) (GIBCO) in 5 ml Teflon vessels containing 0.5 ml of sterile hydrated fluorogenic microspheres (1.2 mmol of substrate/g dry microspheres). Microspheres were removed after 2 hr of incubation at 37° C. in a humidified atmosphere of 5% $CO_2$/95% air for microscopic observation. Photographs were taken using Kodak Ektachrome Film, ASA 400, at 200 X magnification.

Culturing cells on polyacrylamide microspheres derivatized with fluorogenic substrates was based on the principle of cytodex microcarriers (Pharmacia Fine Chemicals, Sweden). A basic factor governing cell attachment and growth is the density of the charges on the culture surface. Cytodex spheres are designed to have an optimal charge density of 1.5 meg/g dry microspheres under standard culture conditions. Best growth of cells in culture occurs when microcarriers have a size distribution which lies within the limits of 100–230 microns in diameter. The microspheres should be transparent and allow an easy microscopic examination of the attached cells. Also, they should be non toxic to the cells.

The polyacrylamide microspheres with immobilized fluorogenic substrates meet the above requirements. The immobilization of the fluorogenic substrate onto the microsphere introduced the required charge density for the optimal cell attachment and growth. This was controlled by the amount of substrate incorporated into the microsphere (1.2 mmol of substrate (or charge)/g dry microspheres.

The ability of primary cultured cells and cell lines to grow on polyacrylamide microspheres derivatized with Cbz-Ala-Ala-Ala-6AQ was evaluated. Human monocytes and embryonic lung fibroblasts (IMR-90) attached and flattened onto the microspheres within 2 and 5 hours, respectively. These results indicate that derivatized polyacrylamide microspheres have no cytotoxic effects and that they provide a convenient surface for cell attachment and growth.

2. Cell Culture on HEMA Gels Copolymerized with Fluorogenic Substrates.

IMR-90 (11th passage) were used for this study. Into each chamber of a Costar cluster dish (6 wells, 1.6 cm diameter) was placed an individual HEMA gel disk copolymerized with the fluorogenic substrate Cbz-Phe-AllylAQ+. To each chamber was added a suspension of cells that contained $5 \times 10^4$ cells in 0.5 ml of DMEM supplemented with 10% fetal bovine serum, penicillin (100 units/ml), and streptomycin (100 g/ml). The cells were allowed to settle directly onto the HEMA disks for 4 hours. The medium then was removed and the gels were transferred to new chambers containing 2.0 ml of medium. The gels then were incubated at 37° C. in a humidified atmosphere of 5% $CO_2$/95% air. Cells were fed three times weekly and photographed at various times (Polariod 667 black and white film). As a control, $5 \times 10^4$ cells were seeded in the manner described above directly onto the tissue culture dish. Cells also were seeded on HEMA gels with no substrate present.

Mouse peritoneal macrophages were harvested following thioglycollate stimulation for 3 days using the method of Conrad *Manual of Macrophage Methodology* (M. Dekker Corp., N.Y., N.Y. 1981) pp. 5–11. The cells were seeded ($5 \times 10^4$ cells/HEMA gel) on the HEMA gels copolymerized with the fluorogenic substrate Bz-DL-Arg-AllylAQ+ (RPMI 1640) in 10% fetal bovine serum. After 2 hours of incubation at 37° C. in 5% $CO_2$/95% air, unattached cells were removed.

Cells were maintained and fed three times a week. Photographs were taken of cells on the HEMA gels and cells that were directly seeded onto the plastic culture dish (Polaroid 667). Human monocytes $5 \times 10^4$ cells/HEMA gel also were seeded onto gels copolymerized with the fluorogenic substrate Cbz-Ala-Ala-Ala-AllylAQ+.

It has been demonstrated (Civerchia-Perez et al., 77 *Proc. Natl. Acad. Sci.* 2064-2068 (1980) that HEMA gels prepared with collagen support the growth of human embryonic lung fibroblasts (IMR-90). IMR-90 cells have been successfully grown on collagen (calf skin)-HEMA gels copolymerized with the fluorogenic substrate Cbz-Phe-AllylAQ+. These gels supported the growth of cells (Figure VII-3A) in the same manner as that of cells grown on collagen-HEMA gels.

Furthermore, the collagen-HEMA gels containing the fluorogenic substrate supported the growth of cells at a level comparable to the respective cells grown on tissue culture surfaces. Microscopic examination also revealed that mouse peritoneal macrophages attached and morphologically retained their shape on HEMA gels containing either collagen or the fluorogenic substrate + collagen. This was also the case with human monocytes.

The results of these experiments showed that immobilized fluorogenic substrates incorporated into biologically inert polymers provide good surfaces for cell adhesion and growth.

EXAMPLE VI: DETECTION OF PROTEINASE RELEASE

Use of Fluorescent Microspheres to Measure Elastase from Monocytes in Culture.

Monocytes were cultured on the Cbz-Ala-Ala-Ala-6AQ microsphere in DMEM medium. Fluorescence microscopy measurements revealed that the microspheres which had been incubated with monocytes for 12 hr showed an increase in fluorescence (4.0 RFU) as compared to those incubated with medium alone (0.6 RFU).

The γGFx of rabbit antiserum raised against human neutrophil elastase was employed to determine whether the fluorescence change observed was due to the release of elastase from monocytes. First, experiments were performed to demonstrate that activity of purified human leukocyte elastase could be inhibited by the γGFx of the antiserum. The soluble substrate, Cbz-Ala-Ala-Ala MAQ+ ($1.0 \times 10^{-4}$ M), and purified human leukocyte elastase were incubated for 20 hr in the presence of the γGFx of antiserum or normal serum. After the incubation, hydrolysis of the substrate was determined by exciting at 410 nm and measuring the emission at 550 nm. In this experiment, approximately 50% of the activity of the enzyme was neutralized by the γGFx of the antiserum (See Table 1 below, which shows the results of neutralization of purified human leukocyte elastase (HLE) by the γGFx of rabbit antiserum against neutophil elastase). When the same experiment was carried out in the absence of human leukocyte elastase, the hydrolysis of the fluorogenic substrate was only 5% compared to samples exposed to the enzyme. The data in Table 1 also indicate an activation of the enzyme in the presence of the γGFx of normal serum. However, it is expected that the activation factor is present in both the γGFxs of normal serum and the antiserum; therefore, their relative difference will remain unchanged.

TABLE 1

Neutralization of Purified Human Leukocyte Elastase (HLE) by the γ-Globulin Fraction (γGFx) of Rabbit Antiserum Against Neutrophil Elastase.*

| Volume of γGFx of Normal Serum or Antiserum Added | HLE Activity (RFU × $10^{-3}$) |
| --- | --- |
| 0 ul γGFx of normal serum or antiserum, no HLE present | 0.5 |
| 0 ul γGFx of normal serum antiserum | 8.6 |
| 10 ul γGFx of normal serum | 9.6 |
| 10 ul γGFx of antiserum | 8.4 |
| 100 ul γGFx of normal serum | 12.0 |
| 100 ul γGFx of antiserum | 6.9 |
| 200 ul γGFx of normal serum | 11.0 |
| 200 ul γGFx of antiserum | 7.0 |

*Each cuvette contained 100 ul of the γGFx of normal serum, 200 ng pf HLE, and $1.0 \times 10^{-4}$ M of the fluorescent substrate Cbz—Ala—Ala—Ala—MAQ*.

Inhibition of the elastase activity of monocytes in culture by the γGFx of the antieserum against neutrophil elastase was determined using Cbs-Ala-Ala-Ala-6AQ polyacrylamide microspheres. Table 2 below shows the results of the effects of different dilutions of the γGFx of normal serum and the γGFx of antiserum on the hydrolysis of the immobilized fluorogenic substrate caused by the human monocytes. As can be seen from Table 2, there is a good correlation between the concentration of the γGFx of the antiserum and the inhibition of monocyte elastase activity. No apparent inhibition was detected at the γGFx of antiserum dilution of 1:100, whereas at the dilution of 1:10 about 50% of the enzyme activity was inhibited.

TABLE 2

Effects of Different Dilutions of the γ-Globulin Fraction (γGFx) of Normal Serum and the γGFx of Antiserum on the Hydrolysis of the Immobilized Fluorogenic Substrate Caused by Human Monocytes.

| Dilutions | Monocytes Samples | Elastase Activity (RFU)* |
| --- | --- | --- |
| 1:10 | γGFx of normal serum | 5.20 |
| 1:10 | γGFx of antiserum | 2.47 |
| 1:50 | γGFx of antiserum | 2.83 |
| 1:100 | γGFx of normal serum | 4.47 |
| 1:100 | γGFx of antiserum | 5.78 |

*Readings were taken after 19 h of incubation.

Figure 3:
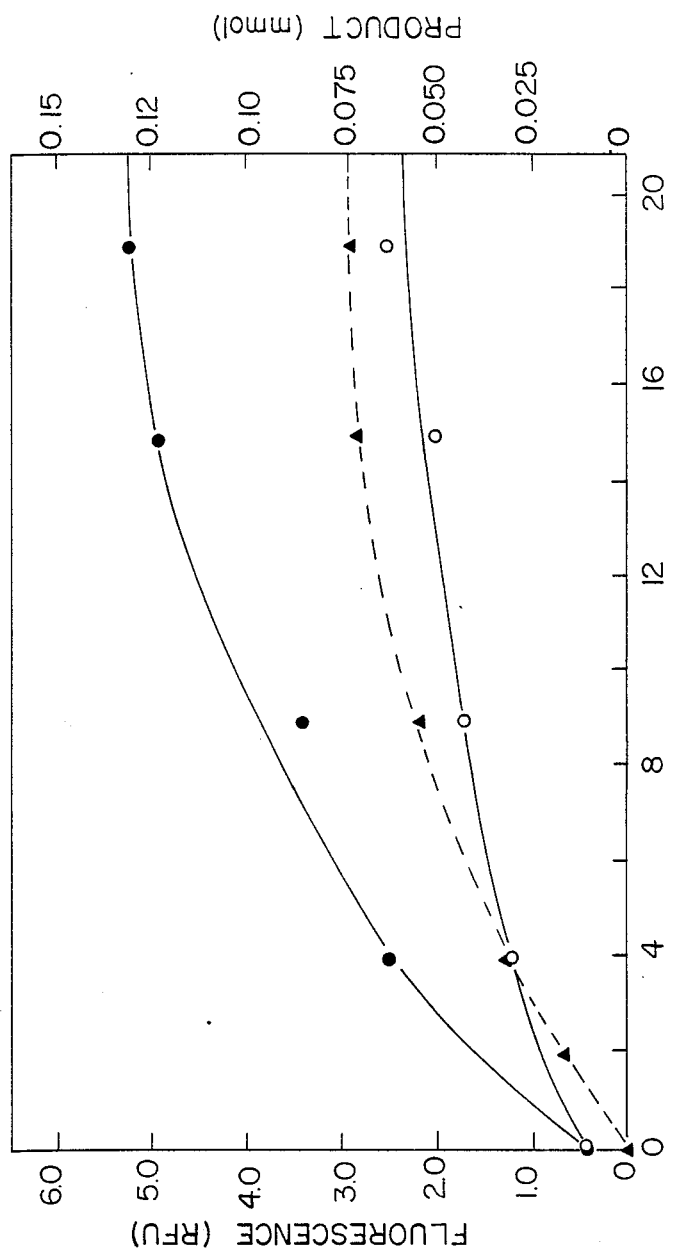

Utilizing the fluorogenic substrate Cbz-Ala-Ala-Ala-6AQ covalently bound to polyacrylamide microspheres, levels of proteinase activity released by cells can be quantified. The results show an increase in the relative fluorescence intensity, which is characteristic of the proteolytic product, as a function of time from human monocytes treated with the γGFx of normal serum. In addition, a significant reduction in the fluorescence intensity was observed in monocytes exposed to the γGFx of rabbit antiserum raised against neutrophil elastase, indicating a specific inhibition of elastase activity. The elastase molecule that interacts with the substrate is primarily released by monocytes, and this release increases with time after the initial attachment of the cell to the microsphere. The results are shown in Table 3 below and FIG. 3, which is a graph of time (hrs.) vs. fluorescence (RFU).

TABLE 3

Hydrolysis of Polyacrylamide Microspheres Derivatized with Cbz-Ala-Ala-Ala-6AQ Caused by Human Monocytes in the Presence of the γ- Globulin Fraction (γGFx) of Normal Serum or the γGFx or Antiserum Raised Against Neutrophil Elastase. *

| Incubation Time (h) | Monocytes Samples* | Elastase Activity (RFU)* |
| --- | --- | --- |
| 4 | γGFx of normal serum | 2.49 |
| 4 | γGFx of antiserum | 1.17 |
| 9 | γGFx of normal serum | 3.35 |
| 9 | γGFx of antiserum | 1.70 |
| 15 | γGFx of normal serum | 4.86 |
| 15 | γGFx of antiserum | 1.98 |
| 19 | γGFx of normal serum | 5.20 |
| 19 | γGFx of antiserum | 2.47 |

*Dilution of γGFx of anitserum and normal serum was 1:10 in all cases.

These experiments clearly demonstrate, for the first time, the feasibility of using a covalently immobilized fluorogenic substrate to visualize directly and to detect the proteinase released from cells in culture.

What is claimed is:

1. An immobilized fluorogenic substrate for identifying and quantifying, intra- and extra-cellularly, the production and secretion of cell-specific enzymes in human and mammalian body fluids as well as in animal extracts, which has the structure:

$R_1$-NH-$R_4$-$R_2$-$R_3$ wherein
$R_1$ represents an oligopeptide which has an amino acid sequence that is enzyme-specific in terms of cleavage of the amino acid sequence at the peptide linkage proximal to a fluorogenic moiety, the oligopeptide comprising naturally occurring amine acids associated with mammalian and bacterial systems, $R_1$ being joined to NH via a carbonyl group in $R_1$;

$R_2$ represents a spacer group which comprises a group having the structural formula $(CH_2X_1X_{2a}(CH_2)_yX_3)$ wherein $X_1$ is CO or $SO_2$; $X_2$ is NH; a is zero or one, provided that when a is zero, $X_1$ is CO; $X_3$ is a member selected from the group consisting of NH, NHCO, CONH, OCO, COO or $Si(O-)_3$; and y is an integer from zero to 15;

$R_3$ represent a glass or polymer having a complementary group which forms an ester or amide linkage with the ω-sulfonic acid or ω-carboxylic acid function of the spacer group or an ether linkage with the ω-carbon atom and hydroxyl group in the polymer; and $NH-R_4$ represents a fluorogenic moiety having a second functional group to which is attached the spacer group, said fluorogenic moiety selected from the group consisting of aminoquinolines and their alkyl and alkoxyl derivatives; alkyl, alkoxyl and carboxyl derivatives of aminonaphthalenes; alkyl, akoxyl and carboxyl derivatives of aminocoumarines; alkyl, alkoxyl and carboxyl derivatives of acridines; and alkyl, alkoxyl, amino, nitro and carboxyl derivatives of benzofurazans.

2. The substrate of claim 1 wherein $R_3$ is selected from the group consisting of polyacrylamide, poly(4-aminostyrene) and glass.

3. The substrate of claim 1 wherein $R_3$ comprises a copolymer of an N-allyl amide with a polymerizable monomer selected from the group consisting of styrene, butadiene, vinyl acetate, acrylic esters, acrylic amides and mixtures thereof, the N-allyl amide being the non-alkylating terminal group of the spacer group.

4. The substrate of claim 1 wherein $R_2$ is selected from the group consisting of $CH_2CONH(CH_2)_5CO$; $CH_2CONHCH_2CH_2NH$; and $CH_2CO$.

5. The substrate of claim 1 wherein $R_1$ is selected from the group consisting of
X-valyl-prolyl-arginyl-Y;
X-(D)-phenylalnyl-picolyl-arginyl-Y;
X-phenylalanyl-valyl-arginyl-Y;
X-glycyl-prolyl-arginyl-Y;
X-valyl-leucyl-lysyl-Y; X-(D)-valyl-leucyl-lysyl-Y;
X-glytamyl-lysyl-lysyl-Y; X-glycyl-proplyl-lysyl-Y;
X-valyl-glycyl-arginyl-Y;   X-glutamyl-glycyl-arginyl-Y;
X-propyl-phenylalnyl-arginyl-Y; X-(D)-prolyl phenylalanyl-arginyl-Y; X-(D)-valyl-leucyl-arginyl-Y;
X-isoleucyl-glutamyl-glycl-arginyl-Y;
X-alanyl-propyl-alanyl-Y;
X-alanyl-alanyl-prolyl-valyl-Y; and
X-alanyl-alanyl-propyl-methionyl-Y; wherein
X is a N-terminal blocking agent or H and Y is a fluorescent amine.

6. The substrate of claim 1 wherein the fluorogenic moiety is selected from the group consisting of
3-amino-quinoline,
2-(N,N-dimethylamino)methyl-6-aminonaphthalene and
4-(N,N-dimethylamino)methyl-6-aminocoumarin.

7. An immobilized fluorogenic substrate for identifying and quantifying, intra- and extra-cellularly, the production and secretion of cell-specific enzymes in human and mammalian body fluids as well as in animal cell extracts, which has the structure:

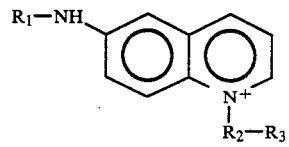

wherein $R_1$ represents an oligopeptide which has an amino acid sequence that is enzyme-specific in terms of cleavage of the amino acid sequence at the peptide linkage proximal to the quinoline ring;

$R_2$ represents a spacer group which comprises a group having the structural formula $(CH_2X_1X_{2a}(CH_2)_yX_3)$ wherein $X_1$ is CO or $SO_2$; $X_2$ is NH; a is zero or one, provided that when a is zero, $X_1$ is CO; $X_3$ a member selected from the group consisting of NH, NHCO, CONH, OCO, COO or $Si(O-)_3$; and y is an integer from zero to 15; and $R_3$ represents a polymer having a complementary group which forms an ester or amide linkage with the ω-sulfonic acid or ω-carboxylic acid function of the spacer group.

8. A process for preparing an immobilized fluorogenic substrate capable of identifying and quantifying, intra- and extra-cellularly, the production and secretion of cell-specific enzymers in human and mammalian body fluids as well as in animal cell extracts which comprises:
  (a) coupling an enzyme-specific oligopeptide to the primary amino group of a fluorescent aminoquinoline via an amide linkage;
  (b) guaternizing the ring nitrogen of the quinoline moiety with an alkylating spacer group selected from haloacetylamino, halo-acetoxy- or halomethylsulfonylamino-polyethylene compounds having an ω-amino (protected), an ω-hydroxyl or ω-carboxylic acid group;
  (c) coupling the ω-functional group of a spacer moiety with the complementary group of the polymer material to form an ester or an amide linkage, which intrinsically immobilizes the peptidyl quinoline assembly.

9. A process for preparing an immobilized fluorogenic substrate capable of identifying and quantifying, intra- and extra-cellularly, the production and secretion of cell specific enzymes which comprises:
  (a) coupling an enzyme-specific oligopeptide to the primary amino group of a fluorescent aminoquinoline via an amide linkage;
  (b) quaternized the ring nitrogen of the quinoline moiety with an allyl group to produce an allylic monomer; and
  (c) copolymerizing the allylic monomer with a second polymerizable monomer in the presence of a radial-generating catalyst, to immobilize the enzyme cleavable substrate.

10. The process of claim 9 wherein the second monomer is selected from the group consisting of hydroxyethyl methacrylate, vinyl chloride, styrene and butadiene.

11. A process for preparing an immobilized fluorogenic substrate capable of identifying and quantifying, intra- and extra-cellularly, the production and secretion of cell specific enzymes which comprises:

(a) coupling an enzyme-specific oligopeptide to the primary amino group of a fluorescent aminoquinoline via an amide linkage;

(b) quaternizing the ring nitrogen of the quinoline moiety with an alkylating spacer group selected from the group consisting of haloacetylamino, haloacetoxy- or halomethylsulfonylaminopolymethylene compounds having an ω-amino (protected), an ω-hydroxyl or ω-carboxylic acid group;

(c) reacting the product of step (b) with an allyl amine using a mixed anhydride coupling technique to produce an allylic monomer; and (d) copolymerizing the allylic monomer with a second polymerizable monomer in the presence of a radical-generating catalyst, to immobilize the enzyme cleavable substrate.

* * * * *

UNITED STATES PATENT AND TRADEMARK OFFICE
CERTIFICATE OF CORRECTION

PATENT NO. : 4,897,444

DATED : January 30, 1990

INVENTOR(S) : Brynes et al.

It is certified that error appears in the above-identified patent and that said Letters Patent is hereby corrected as shown below:

Column 1, line 25, after "cancer" insert --and emphysema for example, the targets of the enzyme action are--

Column 2, line 14, "ably" should read --able--; line 38, delete "or"

Column 3, line 16, "kcatKm" should read --kcat/Km--; line 35, "(1082)" should read --(1982)--; line 37, "peptide" should read --peptide- --

Column 4, line 37, after "et al.," insert --27--

Column 5, line 10, "quantitative" should read --quantitation--; line 31, "Bryness" should read --Brynes--

Column 6, line 64, after "Arg = arginine" insert --Gly=glycine--

Column 7, line 10, after "(N-carbobenzoxy-L-" insert --alanyl--; line 68, "aminoquinolines" should read --aminoquinoline--

UNITED STATES PATENT AND TRADEMARK OFFICE
CERTIFICATE OF CORRECTION

PATENT NO. : 4,897,444

DATED : January 30, 1990

INVENTOR(S) : Brynes, et al.

It is certified that error appears in the above-identified patent and that said Letters Patent is hereby corrected as shown below:

Column 8, line 11, "aminoquinolines" should read --aminoquinoline--; line 13, "quarternized" should read --quaternizing--; line 32, "aminoquinolines" should read --aminoquinoline--; line 40, "quaternized" should read --quaternizing--; line 51, "aminoquinolines" should read --aminoquinoline--; line 53, "quaternized" should read --quaternizing--

Column 9, line 4, "$R_1NH-R_4-R_2-R_3$" should read --$R_1-NH-R_4-R_2-R_3$--

Column 11, line 24, "X-glycyl-proplyl-" should read -- X-glycyl-prolyl- --; line 45, "$CH_2X_1X_2(CH_2)_yX_3$" should read --$CH_2X_1X_{2a}(CH_2)_yX_3$--

Column 12, line 44, "Biocyem" should read --Biochem--; line 57, "6-Ag" should read --6-AQ--

Column 15, line 19, after "proposed" insert --structures.--; line 26, "chloroformmethanol" should read --choloroform/methanol--; line 36, "6µM" should read --67µM--; line 58, "L alanine" should read --L-alanine--; line 58, "L valine" should read --L-valine--

UNITED STATES PATENT AND TRADEMARK OFFICE
CERTIFICATE OF CORRECTION

PATENT NO. : 4,897,444

DATED : January 30, 1990

INVENTOR(S) : Brynes et al.

Page 3 of 5

It is certified that error appears in the above-identified patent and that said Letters Patent is hereby corrected as shown below:

Column 16, line 51, "L arginine" should read --L-arginine--; line 53, "211" should read --217--; line 55, "an" should read --and--; line 67, "6-(N-p-Methoxybenzenesulfonyl L-arginylamino)" should read --6-(N-p-Methoxybenzenesulfonyl-L-arginylamino)--

Column 17, line 13, "6-(N-α-Benzoyl-Nω-methoxybenzenesulfonyl-L" should read --6-(N-α-Benzoyl-Nω-p-methoxybenzenesulfonyl-L--; line 17, "1.48 .mmol" should read --1.48 mmol--; line 46, delete "14"

Column 18, line 49, "63.45" should read --63.45;--; line 67, "$H_2O$;" should read --$H_2O$:--

Column 19, line 16, "6-N-Carbobenzoxy-L-alanyl-L-alanyl L-piolyl" should read --6-N-Carbobenzoxy-L-alanyl-L-alanyl-L-piolyl--

Column 21, line 49, "4.74" should read --5.74--

Column 22, line 33, insert --.-- after test

UNITED STATES PATENT AND TRADEMARK OFFICE
CERTIFICATE OF CORRECTION

PATENT NO. : 4,897,444

DATED : January 30, 1990

INVENTOR(S) : Brynes et al.

It is certified that error appears in the above-identified patent and that said Letters Patent is hereby corrected as shown below:

Column 23, line 11, "quinoline" should read --quinolinium--; line 24, "quinoline" should read --quinolinium--; line 38, "I$^{31}$" should read -- I- --; line 41, "quinoline" should read --quinolinium--; line 50, "ethanol ether" should read --ethanol-ether--; line 51, "45°" should read --145°--; line 53, "M+)" should read --(M$^+$)--; line 59, "48 hr" should read --48 hr.--

Column 24, line 7, "quinoline" should read --quinolinium--; line 14, insert --.-- after test; line 18, "quinoline" should read --quinolinium--; line 42, "Cbz-Ala Ala-ala-" should read --Cbz-Ala-Ala-Ala---

Column 25, line 28, "acrylated" should read --acylated--

Column 27, line 24, "Cbz-Ala-Ala-6AQ" should read --Cbz-Ala-Ala-Ala-6AQ--

Column 29, line 2, "quinoline" should read --quinolinium--

UNITED STATES PATENT AND TRADEMARK OFFICE
CERTIFICATE OF CORRECTION

PATENT NO. : 4,897,444

DATED : January 30, 1990

INVENTOR(S) : Brynes et al.

It is certified that error appears in the above—identified patent and that said Letters Patent is hereby corrected as shown below:

Column 30, line 57, "PBS CMF" should read --PBS-CMF--

Column 31, line 24, "149-1164" should read --1149-1164--;
line 38, "cytodex microcarriers" should read --cytodex-microcarriers--

Column 33, line 8, "Ala-Ala MAQ+" should read --Ala-Ala-MAQ+--;
line 47, "Cbs-Ala-Ala-Ala" should read --Cbz-Ala-Ala-Ala--;
line 67, after "2.47" insert --1:50 $\gamma GF_x$ of normal serum 5.40--

Column 35,
line 23, "aminocoumarines" should read --aminocoumarins--;
line 42, "phenylalnyl" should read --phenylalanyl--;
line 49, "phenylalnyl" should read --phenylalanyl--

Column 36, line 29, "enzymers" should read --enzymes--; line 39, "polyethylene" should read --polymethylene--; line 59, "radial" should read --radical--

Signed and Sealed this

Eleventh Day of June, 1991

Attest:

HARRY F. MANBECK, JR.

*Attesting Officer*　　　　*Commissioner of Patents and Trademarks*

UNITED STATES PATENT AND TRADEMARK OFFICE
CERTIFICATE OF CORRECTION

PATENT NO. : 4,897,444

DATED : January 30, 1990

INVENTOR(S) : Paul J. Brynes and Patricia Andrade-Gordon

It is certified that error appears in the above-identified patent and that said Letters Patent is hereby corrected as shown below:

Column 1, line 5, insert --This invention was made with government support under NIH Grant Nos. 431-E053F; 431-E079G; 431-1741A; GM 29220; and GM-34052 awarded by the National Institutes of Health. The government has certain rights in the invention.--

Signed and Sealed this

Twentieth Day of April, 1993

*Attest:*

MICHAEL K. KIRK

*Attesting Officer*  Acting Commissioner of Patents and Trademarks